United States Patent [19]

Mitsuhashi et al.

[11] Patent Number: 5,290,691
[45] Date of Patent: Mar. 1, 1994

[54] SAFE AND VERSATILE CLONING VECTOR

[75] Inventors: Susumu Mitsuhashi, Tokyo; Matsuhisa Inoue, Gunma; Masao Nagashima, Saitama, all of Japan

[73] Assignee: Banyu Seiyaku Kabushiki Kaisha, Tokyo, Japan

[21] Appl. No.: 814,203

[22] Filed: Dec. 26, 1991

Related U.S. Application Data

[63] Continuation of Ser. No. 628,924, Dec. 11, 1990, abandoned, which is a continuation of Ser. No. 914,149, Oct. 1, 1986, abandoned.

[30] Foreign Application Priority Data

Oct. 1, 1985 [JP] Japan ................. 60-216209

[51] Int. Cl.$^5$ ............ C12N 15/00; C12N 15/11; C12N 15/70; C12N 15/74
[52] U.S. Cl. ............ 435/252.31; 435/252.33; 435/252.34; 435/172.1; 435/320.1; 435/172.3; 536/23.1; 935/27; 935/29
[58] Field of Search ............ 536/27; 435/172.1, 172.3, 435/252.31, 252.33, 252.34, 320.1; 935/27, 29, 38, 41

[56] References Cited

U.S. PATENT DOCUMENTS

| | | | |
|---|---|---|---|
| 4,376,164 | 3/1983 | Olsen | 435/172 |
| 4,514,502 | 4/1985 | Miwa | 435/253 |
| 4,657,858 | 4/1987 | Davison | 435/68 |
| 4,745,069 | 5/1988 | Mayne | 435/320 |

FOREIGN PATENT DOCUMENTS 0162725 5/1985 European Pat. Off. ..... C12N 15/00

OTHER PUBLICATIONS

Ishiwa, H. et al. *Gene* 32 (1984) 129-134.
Bagdasarian, M. et al. *Gene* 16 (1981) 237-247.
Schmidhauser T. J. et al. 1985 "Regions of Broad-Host Range Plasmid Rk-2 Involved in Replication & Stable Maintenance in Nine Species of Gram-Negative Bacteria" J. Bact. 164(1) 446-455.
Thomas C. M. 1982 "Maintenance of Broad Host Range Plasmid RK-2 Replicans in *Pseudomonas-aeruginosa*" Nature 298(5875) 674-676.
Smith C. A. et al 1985 "Comparison of the Nucleotide Sequences of the Vegetative Replication Origins of Broad Host Range In cP Plasmids R751 & RK2 Reveals Conserved Features" NAR 13:557.
Laporta, M. Z. et al. 1986 Plasmids Coding for Drug Resistance and Localized Adherence to HeLa Cells in *E. coli* Infect. Imm. 51(2): 715.
Ishiwa H. (1985) Newshuttle Vector for *E. coli* and *B. subtilis* III Jap. J. Geract 60(5) 485-498.
Band L. (1983) "Construction of a Vector for Cloning Promoters in *B. subtilis*" Gene 26(2-3) 313-15.

*Primary Examiner*—Robert A. Wax
*Assistant Examiner*—D. Cook
*Attorney, Agent, or Firm*—Young & Thompson

[57] ABSTRACT

A safe and versatile recombinant DNA cloning vector having at least two functionally different replication origins selected independently from the group consisting of a replication origin functional in *Bacillus subtilis*, a replication origin functional in *Escherichia coli* and a replication origin functional in *Pseudomonas aeruginosa*, and at least one DNA segment which provides resistance against at least one antibiotic after introduction into susceptible host cells. The origin for replication origin functional in *Bacillus subtilis* can be a restriction fragment of a plasmid of Gram positive bacteria, and that *Escherichia coli* or *Pseudomonas aeruginosa* can be a restriction fragment of a plasmid of Gram negative bacteria, e.g. a restriction fragment of plasmids pMS 140-1 or pMS 71.

8 Claims, 10 Drawing Sheets

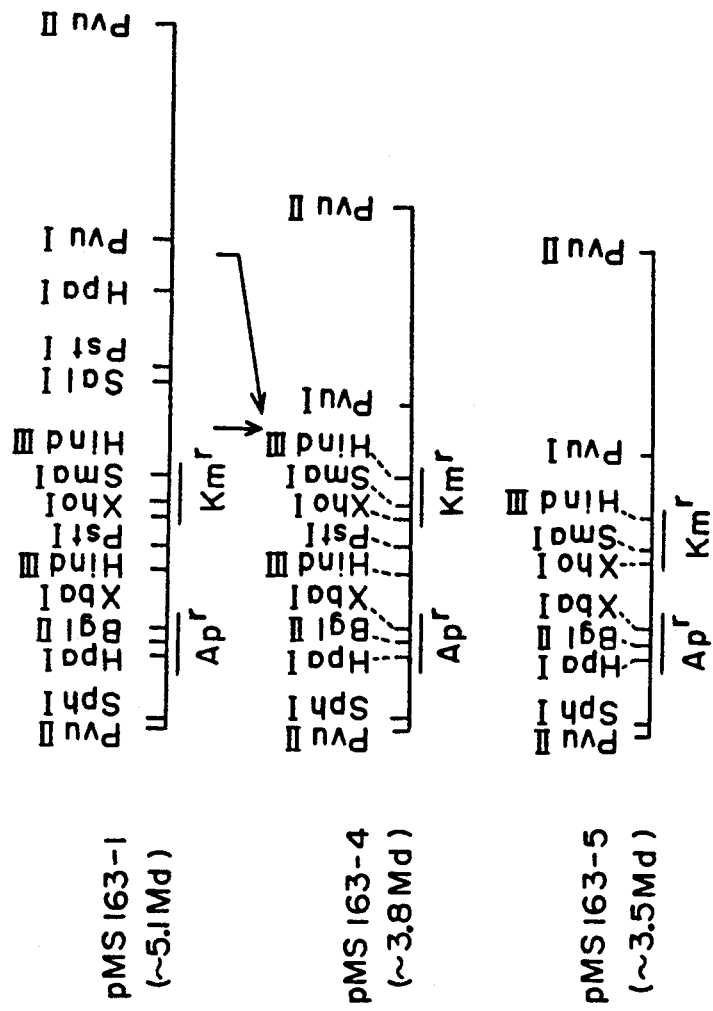

SAFE AND VERSATILE CLONING VECTOR

This application in a continuation of application Ser. No. 07/628,924, filed Dec. 11, 1990, now abandoned, which is a continuation of Ser. No. 06/914,149 filed Oct. 1, 1986, now abandoned.

FIELD OF THE INVENTION

The present invention relates to a safe and versatile cloning vector containing a replication origin functional in *Bacillus subtilis* (hereinafter designated as Bacillus), a replication original functional in *Escherichia coli* (hereinafter designated as *E. coli*) and a replication origin functional in *Pseudomonas aeruginosa* (hereinafter designated as Pseudomonas), and one or more DNA segments which provide resistance against antibiotics to a bacterial cell transformed with said vector.

BACKGROUND OF THE INVENTION

Many kinds of cloning vectors exist. However, no versatile cloning vector which can be functional in different microorganisms such as in Bacillus, *E. coli* and Pseudomonas has generally been known. Such a versatile cloning vector functional only in Streptomyces, Bacillus and *E. coli* (Jap. Pat. Unexam. Publ. No. 58-134100) or in Corynebacterium and Brevibacterium (ibid. No. 58-105999) is known.

An object of the present invention is to provide novel versatile cloning vectors which can be functional in Bacillus, Pseudomonas and *E. coli* and which can include one or more drug resistance genes in each of these microorganisms.

The importance of vectors to genetic engineering is described in *Recombinant Molecules; Impact on Science and Society*, Miles International Symposium Ser. No. 10, Ed. by R. F. Beers, Raven Press, New York (1977).

In *E. coli*, plasmid vectors such as pBR 322 have often been used. The numerous advantages of plasmid vectors like pBR 322 are as follows:

(1) a high copy number in bacterial cells;

(2) a low molecular weight and limited number of sites for restriction endonuclease cleavage provide an essential simplicity for cloning foreign DNA fragments while retaining replication activity;

(3) bacterial cell populations which contain selectable markers such as ampicillin- and tetracycline-resistance genes and the ability to easily isolate large quantities of plasmid have made plasmid vectors the most useful to date;

(4) the insertion of foreign DNA into restriction enzyme cleavage sites of a plasmid, i.e. the PstI site in ampicillin-resistant genes and BamHI, HindIII and SalI sites in tetracycline-resistant genes, transforming drug-resistance to drug-sensitivity due to breakage of the resistant genes, provides easy selection of recombinant DNA holding bacteria by selecting plasmid holding cells with one drug resistant nature, while selecting susceptibility to another drug. [F. Boliva et al., Gene, 2, 95 (1977)].

Many different types of plasmid vectors have been prepared for *E. coli* and other industrially useful bacteria, for example, the amylase-producing bacteria Bacillus, and the waste decomposing strain Pseudomonas. Unfortunately, however, no easily manipulable plasmid vector as compared with those in *E. coli* has been found in Bacillus or Pseudomonas. Plasmid replication and gene expression are restricted to and affected by background factors in transformed cells. For example, transduction of a drug resistance gene of *E. coli* ligated to a plasmid of Bacillus and transformed into Bacillus will replicate its recombinant plasmid, but cannot express the drug resistance element derived from *E. coli*. [J. Kreft et al., Mol. Gen. Genet., 162, 59 (1978); J. L. Schottel et al., J. Bacteriol., 146, 360 (1981).] Additionally, because of the lack of a Pseudomonas specific origin of replication, the *E. coli* plasmids pBR 322 and pACYC 184 cannot transform Pseudomonas. [*Plasmid Medical, Environmental and Commercial Importance*, K. N. Timmis and A. Puhler, Eds., pp 411-422].

Plasmid vectors pBR 322 or pCRI, which possess the replication origins of pMBI or ColEI, were originally non-transferable plasmids. However, they can be transferred together with a coexisting transferable and another third non-transferable plasmid. [Current Chemoth. and Immunotherapy, Proc. 12th Inter. Cong. Chemoth., Vol. 1, p. 6.] These vectors are not preferable from a safety point of view, because it may be dangerous to transfer a drug resistance gene in a vector and an unknown gene in a recombinant.

Plasmid vectors developed in *E. coli* are, in their replication origins, limited to ColEI, pMBI, p 15A and R 6-5. When an insertion of plural plasmid vectors in a cell is required in order to increase productivity and to investigate gene relation, there may occur incompatibility, namely such like vectors cannot coexist stably in a host cell and are eliminated.

A vector, RP-4, often used in Pseudomonas, is a large, transferable plasmid of molecular weight 38Md. It is not a preferred vector, because the genetic information required for RP-4 replication is located on a separate plasmid molecule and hence the preparation of a smaller vector plasmid is difficult. Only the plasmids RSF 1010 and Rlb 679 (5.5Md) have been reported; however, they are not preferred because insertional inactivation cannot be carried out using easily handled restriction enzymes.

Bacillus has the following advantages:

(1) it is a production strain of antibiotics butyrocin and polymyxin;

(2) it is a production strain of amylase and protease;

(3) it is an important industrial strain for exoenzymes; and (4) it is non-parasitic in humans and therefore safe for receipt of foreign DNA.

Regrettably, vector development has not progressed as far or as quickly in Bacillus as it has in *E. coli*. One reason for this is that the multiple drug resistance genes of *E. coli* cannot be expressed hence in Bacillus, and hence resistance markers of *E. coli* cannot apply to Bacillus. Furthermore, the effectiveness of transformation using competent cells is much lower at $10^2$-$10^3$ transformants per 1 μg of DNA as compared with that of the *E. coli* series at $10^8$ to $10^{12}$ transformants. Alternatively, Bacillus transformation by protoplast fusion improved the yield of transformants but requires time and practice, so that development of a drug marker having a preferred restriction site applicable to insertional inactivation might be delayed. Shuttle-vectors of Bacillus and *E. coli* have been reported [Abstract, Jap. Agr. Biol. Chem. Soc. Meeting 1980, p. 408], but unlike *E. coli* vectors the recombinant DNA technique for Bacillus expression of resistance against more than one kind of drug cannot be observed and so no insertion-inactivation method is used.

BRIEF DESCRIPTION OF THE INVENTION

As a result of the investigation of the drug-resistant gene markers which can be expressed in Gram positive bacteria like Bacillus, Gram negative bacteria like Pseudomonas and *E. coli*, having easily selected the plasmid carrying strains, it has been found that the replication part of plasmid pMS 71 from *Proteus mirabilis* and that of plasmid pMS 140-1 from *Bacillus cereus* covalently joined within the same plasmid can be replicated in Gram positive and negative bacteria, and further that the drug resistance from Gram positive bacteria linked with the same plasmid can also be expressed in each strain.

A novel plasmid of the present invention has the following advantages:

1. It can be replicated in a wide range of host cells. Thus, effective selection of host cells that reveal good expression in one vector, and selection of genes and genetic products from various origins, can be achieved.
2. Two kinds of drug resistance are expressed in any host cells. Selection of plasmid-borne cells and insertional-inactivation can be used, thus simplifying the screening of recombinant plasmid-borne cells.
3. Transformation into the *E. coli* and Bacillus systems is uncomplicated and highly efficient, and thereafter transformation to the desired host is possible.
4. The vectors are of large copy number, more easily isolated and smaller in size.
5. The vectors are safe, namely, not mobilizable between any coexisting plasmids.
6. There are multiple, unique restriction enzyme recognition sites, especially in drug resistance genes for obtaining recombinant plasmid-borne cells.
7. It stably exists in host cells together with *E. coli* vectors pCR 1, pBR 322, pACYC 184, pSC 101 or PBM 9.
8. Drug-resistant genes with high selective toxicity are used as a selected marker.
9. The activity of the selected marker is measured by the amount of enzyme.

Plasmid vectors of the present invention have been deposited in the Fermentation Research Institute, Japan and have been assigned permanent deposit numbers as follows:

*Escherichia coli* ML4901-pMS 163 (Ap$^r$Sa$^r$) FERM P-8288

*Escherichia coli* ML4901-pMS 163-2 (Ap$^r$Km$^r$) FERM P-8289

*Escherichia coli* ML4901-pMS 163-5 (Ap$^r$Km$^r$) FERM P-8290

*Escherichia coli* ML4901-pMS 505-1 (Ap$^r$Sm$^r$) FERM P-8291

*Escherichia coli* ML4901-pMS 504 (Ap$^r$TC$^r$) FERM P-8292

*Escherichia coli* ML4901-pMS 506 (Sm$^r$TC$^r$) FERM P-8293

The advantage of the present invention is that it provides a plasmid vector useful for genetic engineering in host cells of genera Bacillus, Pseudomonas and Escherichia. According to the advantages of the present invention, genes which can express in eucaryote and procaryote cells are cloned in vitro, and thereafter transformed into *Escherichia coli, Pseudomonas aeruginosa, Pseudomonas putida,* and *Bacillus subtilis* to select effectively the desired transformed cells. More particularly, among the advantages of the present invention is that plasmid vector-borne cells can easily be selected by providing one or more drug resistances to host cells. It is therefore possible to select streptomycin-sensitive cells by insertion of DNA into the EcoRI or HindIII site of a streptomycin-resistant gene, and further to select ampicillin-sensitive bacteria by inserting DNA into the PstI or BglII site. By this process plasmid-borne cells are selected with one antibiotic agent; and thereafter, by checking sensitivity to another drug, recombinant plasmid-borne cells can be selected.

A vector of the present invention can be constructed by combining (1) a replication origin functional in Bacillus, (2) a replication origin functional in *E. coli* and Pseudomonas, (3) DNA segments which provide antibiotic resistance to *E. coli* and Pseudomonas, and (4) DNA segments which provide antibiotic resistance to Bacillus, *E. coli* and Pseudomonas. Combining (2) and (3) hereinabove provides a plasmid which can replicate in *E. coli* or Pseudomonas, expressing antibiotic resistance in each. The combination of a plasmid obtained by ligating (1) and (2) with the above DNA segment (4) provides a plasmid which can replicate in *E. coli*, Bacillus or Pseudomonas and can express antibiotic resistance in any of *E. coli*, Bacillus and Pseudomonas.

DNA segments which can be replicated in Bacillus may have originated from eucaryotes and procaryotes, and are preferably plasmids of procaryote, especially Gram positive bacteria, selected from Staphylococcus, genus Streptococcus, genus Corynebacterium, genus Clostridium, genus Brevibacterium, genus Bacillus or Actinomycetes, and phage.

DNA segments which can be replicated in *E. coli* and Pseudomonas may be any plasmids originating from eucaryote and procaryote cells, and are preferably procaryote plasmids, especially Gram negative bacteria, selected from genus Escherichia, genus Pseudomonas, genus Klebsiella, genus Salmonella, genus Alcaligenes, genus Flavobacterium, genus Enterobacter, genus Citrobacter, genus Haemophilis, genus Neisseria, genus Shigella, genus Acinetobacter, genus Campylobacter, genus Vibrio, genus Proteus, genus Serratia or Ercinia, and phage. Any plasmid of one replication origin which can replicate in both *E. coli* and Pseudomonas, or any plasmid, either artificially or naturally ligated with a segment from a replication origin in *E. coli* and that in Pseudomonas can be used. Plasmids which carry antibiotic resistance markers and have selectivity in any of Bacillus, *E. coli* and Pseudomonas, from eucaryotic and procaryotic cells, can be used in the present invention. Preferred examples are DNA segments which carry resistance markers to procaryotes, especially Gram positive bacteria, which are resistant to antibiotics such as β-lactam antibiotics, aminoglycosides, tetracyclines, chloramphenicol and macrolides. However, any type of selection such as resistance to heavy metals and auxotrophic nature can also be used.

A vector of the present invention which carries resistance to tetracycline, ampicillin, streptomycin, kanamycine or sulfa drugs, is preferred for checking the maintenance of the plasmid vector in host cells. Bacterial cells containing recombinant plasmids can easily be screened by incubation in a medium which contains tetracycline, ampicillin, streptomycin, kanamycin or a sulfa drug. Furthermore, bacteria carrying recombinant DNA can be stably maintained in a medium containing a suitable concentration of antibiotic.

Certain Pseudomonas are known to decompose various types of compounds such as the following:

(a) Organic halogen compounds which are widely used as solvents, fire extinguishers, insulators and pesticides, and are difficult to decompose microbiologically, often producing highly toxic byproducts. See *Assimilation of DL-2-chloropropionate,* J. Bacteriol., 150, 522 (1982).

(b) Aromatic compounds which are difficult to decompose. See *Assimilation of n-octane,* Proc. Jap. Agr. Chem. Soc., 1983.

(c) Biphenyl-type compounds in lignin. See *Decomposition of 5,5-dehydrodibenylic acid,* Proc. Jap. Agr. Chem. Soc., 1983.

(d) Azo-dyes. See *Assimilation of p-amino azobenzene,* Euro. J. Appl. Microbiol., 12, 189 (1981).

(e) Methanol. See Molec. Gen. GENET., 178, 375 (1980).

The versatile cloning vector of the present invention can be cloned with a gene of Pseudomonas, which produces various kinds of decomposing enzymes on compounds which are difficult to decompose otherwise, or a gene of Bacillus, which produces useful enzymes such as amylase and protease, and the said cloned plasmid can be expressed in the host cells such as any microorganisms of *E. coli,* Bacillus and Pseudomonas. Namely, the decomposition of compounds which cannot easily be decomposed, and the production of useful substances, can be achieved in desired microorganisms.

As explained hereinbefore, vectors of the present invention have a number of advantages. Namely, the copy numbers of plasmids are high, cloned vectors carry only one restriction enzyme recognition site, cloning of DNA segments can be achieved without loss of replication activity, and tetracyclin resistance, streptomycin resistance, ampicillin resistance, kanamycin resistance or sulfa drug resistance can be used as a selection marker, whereby the screening of plasmid-borne cells is quite easy. The sole restriction enzyme recognition sites of a plasmid are XbaI, BglII and PstI in the ampicillin resistance gene, XhoI, ClaI, SmaI and HindIII in the kanamycin resistance gene, PstI in the sulfa drug resistance gene, or EcoRI and HindIII in the streptomycin resistance gene. Because of such existing restriction enzyme recognition sites in the cloned plasmid, the cloning of DNA segments can be easily achieved without hindering DNA replication activity, and the selection of recombinants can be performed by insertional inactivation.

A vector of the present invention can be transformed in any microbial cells of Bacillus, *E. coli* or Pseudomonas which are sensitive to an antibiotic that is formed in the vector as a resistant gene; and hence ampicillin resistance, kanamycin resistance, sulfa drug resistance and streptomycin resistance are expressed in both of *E. coli* and Pseudomonas, or ampicillin resistance, tetracycline resistance and streptomycin resistance are expressed in any bacterial cells of Bacillus, *E. coli* or Pseudomonas. Therefore, screening of the plasmid vector holding cells in any microorganism cells is easier, and selection of recombinant by insertional inactivation is also quite easy. Thus, a vector of the present invention has the advantage of selecting host cells for the production of a genetic engineering product.

In order to maintain safety during gene manipulation, the spread of recombinant gene and drug resistance in plasmids should be prevented. The plasmid vector of the present invention is not self-transferable, cotransferred with a transferable plasmid, or cotransferred in the presence of three transferable plasmids. Hence, compared to plasmids pBR 322 or pCRI, which are transferred with the aforesaid members, the vectors of the present invention can be said to be safe.

Furthermore, drug resistance markers, e.g. sulfa drug resistance, of the present invention are conversions of heat-labile dihydropteroate synthetase, and are different from the conversion of heat-stable enzymes of sulfadrug resistance in prior known chromosomes, and hence are quite safe.

Moreover, the plasmid vectors of the present invention are quite useful in view of their incompatibility in the host cells *E. coli.* Conventional plasmid vectors used in *E. coli* at present originate from ColEI, pMBI, p15A or R6-5 in their replication origin, for example vector plasmid pCRI, pBR 322, pACYC 184 and pSC101; and the plasmid vector of the present invention can coexist stably in *E. coli* host cells, i.e. different incompatibility groups. Therefore, in order to increase the genetic product, in case many kinds of plasmid in one host cell are required, (for example, if the product is produced through multiple steps of multiple enzymatic action, the same multiple numbers of plasmid vectors which coexist stably are required), the plasmid vector of the present invention is preferable. Also, the analysis of gene interaction can be advantageously effected.

To obtain the versatile plasmid vectors of the present invention, there are cultured the plasmid-supplying bacteria such a *E. coli* and Bacillus in a medium. Supplier microorganisms such as *Escherichia coli* ML4901, *Bacillus subtilis* CRK3000, *Pseudomonas putida* Tn1126 or *Pseudomonas aeruginosa* PA02142 are cultured in a conventional medium containing carbon sources such as molasses, glucose, dextrin and glycerol, nitrogen sources such as soybean powder, peptone and amino acid mixtures, inorganic salts such as a salt of sodium, potassium, calcium, ammonium and magnesium or phosphates, chlorides and sulfates, and trace essential elements for microorganism growth.

As illustrated hereinbefore, examples of microorganism strains used as plasmid host cells in the present invention are *Escherichia coli* ML4901, *Bacillus subtilis* CRK3000, *Pseudomonas aeruginosa* PA02142 and *Pseudomonas putida* Tn1126. Examples of medium and culture conditions are illustrated below, but are only meant as guidelines and can be modified.

Harvesting of bacteria:

1. *Escherichia coli, Psuedomonas aeruginosa* and *Pseudomonas putida* are cultured as follows:

a. Liquid medium for growth of microorganisms and isolation of plasmid.

| L-broth: | Bacto-tryptone | 10 g |
|---|---|---|
| | Yeast extract | 5 g |
| | NaCl | 5 g |
| | Glucose | 1 g |

Dissolve in 1 lit. of deionized water, heat and adjust pH to 7.4 with sodium hydroxide after cooling, then sterilize at 120° C. for 20 min.

b. Agar medium:

Lactose-bromthymol blue (Lac-BTB) agar medium:

| Meat extract | 10 g |
|---|---|
| Peptone | 10 g |
| NaCl | 5 g |
| Lactose | 10 g |
| Agar | 15 g |

| -continued | |
|---|---|
| Bromthymol blue | 0.8 g |

Dissolve in 1 lit. of deionized water, heat, and adjust pH to 7.4 with NaOH after cooling, then sterilize at 120° C. for 20 min.

*Bacills subtilis* is cultured as follows:

a. Liquid medium:

Antibiotic medium 3 (Bacto-Pennasay medium) (Difco)

17.5 g dissolved in 1 lit. of deionized water and sterilized at 120° C. for 15 min.

b. Agar medium:

Heart infusion agar medium (Nissui Co.) 25 g, dissolved in 1 lit. of deionized water with heating and sterilized at 120° C. for 20 min.

Small culture: in 10 ml of broth in test tube.

Large culture: in 100 ml of broth in Sakaguchi flask.

Culture temp.: 30°-37° C.

Plasmid is isolated from the thus-cultured cells by a conventional method according to the following procedure:

Isolation of plasmid: (cleared lysate method)

(1) Bacterial cells in L-broth (200 ml) are shake cultured at 37° C. overnight.

(2) Centrifuge at 6,000 r.p.m. at 4° C. for 15 mins. to collect bacterial cells.

(3) Resuspend cells in a mixture (30 ml) of 10 mM Tris-1 mM EDTA (pH 8.0), transferred into a 50 ml centrifugal tube, followed by centrifugation at 6000 r.p.m. for 10 mins.

(4) Suspend completely the precipitate in cold 25% (w/v) sucrose solution (10 ml) [sucrose (25 g) is dissolved in 100 ml 50mM Tris-1 mM EDTA solution (pH 8.0)].

(5) Ribonuclease (RNase) is added (final concentration: 20 μg/ml) and the mixture is stirred at maximum speed in a Bortex-mixer for 2 min.

(6) Freshly prepared 1% lysozyme solution (1 ml) is added, shaken well, then the mixture is incubated ice cold for 5 min.

(7) Add 0.5 M EDTA (pH 8.0) (2.0 ml), shake well, allow to stand for 10 mins. under ice cooling.

(8) Add cold triton lytic mixture (16 ml), gently revolve test tube with twice turning upside down, mixed gently, ice cold for 15 min.

(9) Centrifuge at 30,000 r.p.m. at 4° C. for 20 min.

(10) Gently transfer the supernatant into a sterilized measuring cylinder.

(11) Add polyethylene glucose (#6,000) up to 10% (w/v) and mix well, thereafter add 1/9 volume 5 M NaCl, then store at 4° C. overnight.

(12) Centrifuge at 5,000 r.p.m. at 4° C. for 10 min. Discard supernatant, add 1/10 diluted SSC solution (SSC: 0.15 M NaCl and 0.015 M sodium citrate) (5 ml) and gently dissolve the DNA.

(13) Gently mix cesium chloride 5 g and DNA sample 5 ml.

(14) After complete dissolution, add 0.1 ml ethidium bromide (10 mg/ml) and 0.1 ml 1/10 diluted SSC solution.

(15) Centrifuge at 37,000-40,000 r.p.m. for 35-40 hours at 20° C.

(16) Stop centrifugation without applying the brake; pick up gently the centrifugal tube and radiate ultraviolet light through a side of the tube to observe the fluorescence of DNA.

(17) Collect the fluorescent band of ethidium bromide with an injection needle inserted into the side of the tube. Be careful not to contaminate the withdrawn band with any other band.

(18) Add an equal amount of cesium-chloride-saturated isopropanol to the DNA sample, shake gently to remove ethidium bromide. Repeat the same operation 3-4 times.

(19) Discard the resultant scarlet colored supernatant solution. Transfer the DNA sample into a dialysis tube, then dialyze against 1/10 diluted SSC solution.

(20) Store the thus-prepared DNA.

(1) Isolation from *E. coli*:

Follow the above procedure. Refer to *Assay Method for Drug Susceptibility*, S. Mitsuhashi Ed., pp. 42-48.

(2) Isolation from Bacillus:

Follow the above procedure, but in (7) hereinabove, cooling for 10 minutes is replaced by heating at 37° C. for 30 minutes.

(3) Isolation from Pseudomonas:

Follow the above procedure, but in (67) hereinabove 1% lysozyme solution is used, and in (7), 0.5 M EDTA addition is not done.

(4) Isolation of plasmid from the above strains can be simplified according to the method described in *Nucleic Acids Research*, Vol. 1, No. 6 (1979) pp. 1511-1523, which is summarized as follows:

Isolation by simple method:

(a) Culture overnight in a suitable medium.

(b) Collect the broth (1.0-1.5 ml) in a 1.5 ml Eppendorf tube and centrifuge at 10,000 r.p.m. for one min. to collect the cells. Discard the supernatant.

(c) Add lysozyme solution (hereinafter referred to as solution 1) 100 μl, agitate the cells with a Bortex mixer and ice cool the material without agitation for 30 min.

(d) Add alkaline SDS solution (hereinafter referred to as solution 2) (200 μl, mix by repeatedly inverting the Eppendorf tube, and allow to stand on ice for 5 min.

(e) Stir with mixing 3M sodium acetate solution (pH 4.8) (hereinafter referred to as solution 3) 150 μl, and allow to stand on ice for 60 min.

(f) Centrifuge at 10,000 r.p.m. for 5 min., collect the supernatant solution (approx. 400 μl). Add twice the volume of 99.5% ethanol, stir and allow to stand at −20° C. for 30 min.

(g) Centrifuge at 10,000 r.p.m. for 3 min. and discard the supernatant solution. Add 100 μl 100 mM sodium acetate-50mM Tris-HCl buffer (pH 8.0) to the precipitate to dissolve the same. Add twice the volume of 99.5% ethanol, stir and allow to stand at −20° C. for 5 min.

(h) Centrifuge at 10,000 r.p.m. for 3 min. Discard supernatant solution and lyophilize. Add 100 μl 1/10 diluted SSC solution to prepare the sample for transformation and agarose gel electrophoresis.

Transformation of the recombinant DNA plasmid can be performed by modified conventional means, as follows:

Transformation:

1. *E. coli*

*E. coli* is cultured in L-broth overnight.

Cultured broth (0.1 ml) is inoculated in fresh L-broth (10 ml) and shake cultured at 37° C. for 3.5 hours. The collected cells are washed with 5 ml 10 mM NaCl-10 mM Tris-HCl buffer solution (pH 8.0). The washed cells are suspended in 5 ml 75 mM CaCl$_2$-10 mM Tris-HCl buffer solution (pH 8.0) and allowed to stand at room temperature for 20 mins. Repeat the same operation and allow to stand on ice to obtain competent cells.

Cold competent cells (200 μl) and plasmid solution (20 μl) are mixed, ice cooled for 20 mins., warmed at 42° C. for 2 mins. followed by adding L-broth (1 ml) then shake cultured at 37° C. for 90 mins. After centrifugation at 3,000 r.p.m. for 10 mins., the cells are washed with BSG solution (1 ml), then resuspended in BSG solution (1 ml). 0.1 ml thereof or its diluted suspension (0.1 ml) is spread on a BTB agar medium containing kanamycin 12.5 μg/ml, and incubated at 37° C. for 24 hours for transformation. For further details, refer to Mitsuhashi, S. Ed. *Assay Methods for Drug Susceptibility*, pp. 38–41.

2. Bacillus:

Bacterial cells are inoculated in Bacto-Pennasay medium (5 ml) with added glucose 0.5% overnight. The collected cells are suspended in C-1 medium (0.5 ml), and 0.2 ml thereof is inoculated in C-2 medium (20 ml) and harvested at 37° C. until the late logarithmic phase of growth, which is transferred to C-2 medium (80 ml), then weakly cultured at 30° C. for 2 hours. The competent cells are collected, suspended in ice cold C-3 medium (10 ml), fractionated into fractions which are each 0.2 ml and stored at −80° C.

The competent cells (0.2 ml) are mixed with C-1 medium (1.8 ml) 20 mM magnesium chloride is added. The said cell mixture (450 μl) is mixed with the plasmid solution (50 μl), incubated at 37° C. for 30 mins. and spread on an agar plate medium containing the drug to achieve transformation. If incubation time is required for expression, the centrifugally collected cells are harvested in Bacto-Pennasaymedium at 37° C. for 1.5 hours and spread on drug-containing agar plates. Refer for further detail to J. Bacteriol., 98, pp. 1239–1247 (1969).

The compositions and preparations of the above C-1, C-2 and C-2 media are as follows:

C-1 medium:

Ammonium sulfate 160 mg., dispotassium hydrogen phosphate 480 mg, sodium citrate 80 mg are dissolved in deionized water 75 ml and sterilized under pressure. To the said solution are added sterilized 10% magnesium sulfate solution 0.16 m, 25% glucose 1.6 ml, 5 mg/ml histidine, adenine and methionine, 0.4 ml each, and 5 mg/ml leucine 0.16 ml.

C-2 medium:

In C-1 medium, histidine, adenine, methionine and leucine are replaced by 10% casamino acid 0.16 ml (pH 7.0) and 5 mg/ml histidine (1.6 ml).

C-3 medium:

In C-1 medium, histidine, adenine, methionine and leucine are replaced by glycerol added up to a final concentration of 5%.

3. *Pseudomonas aeruginosa* and *Pseudomonas putida:*

Bacterial cells grown in the middle logarithmic phase of growth in L-broth (10 ml) are collected by centrifugation, washed with 0.1M magnesium chloride solution (5 ml) and collected. Cells resuspended in 0.1M magnesium chloride (5 ml) are allowed to stand on ice 20 mins., then collected by centrifugation. Cell pellets are suspended in 0.1M magnesium chloride (1 ml) to obtain competent cells.

The competent cells (200 μl) and plasmid solution (50 μl) are mixed, allowed to stand on ice for 60 mins., thereafter warmed at 42° C. for 2 mins., L-broth (1 ml) is added therein, and the cells are harvested at 37° C. for 90 mins. The centrifugally collected cells are washed twice with BSG, BSG (0.5 ml) is added thereto, and the material is spread on drug-containing Lac-BTB agar medium, which is cultured at 37° C. to effect the transformation. Refer for further details to *Antimicrobial Agents and Chemotherapy*, Sept. 1982, pp. 358–363.

Checking for transformation can be performed by conventional means as follows:

Check points after transformation:

(1) Transformation is screened by a resistant marker in a vector.

(2) Check whether there is the desired drug resistance. In general, each test organism is spread on an agar plate medium containing drugs and its growth observed. Single colonies are selected twice on a plate containing the drug.

(3) Isolate DNA by the above simple method, check for molecular size on agarose-gel, electrophorese and remove contaminants. An object DNA is re-transformed to confirm the existence of the target gene marker on a plasmid. If necessary, check by cleaving with a restriction enzyme.

(4) Isolate DNA by the cleared lysate method for large scale preparation. Re-check by agarose-gel.

(5) For the next step in the process, use DNA prepared in (4) above.

The restriction enzyme and other enzymes used in molecular cloning are commercially available.

The isolated plasmid can be modified to a required plasmid for the practice of the present invention by any generally recognized genetic engineering process. The preparation of the plasmid of the present invention is illustrated as follows:

Preparation of pMS 500:

pMS 140-1 is cleared at the outer side of the $Tc^r$ region by the restriction enzyme EcoRI at a single site. pMS 71-17 is $Ap^r$ $Sa^r$. Both plasmids are completely digested by EcoRI to linear sequences, which are treated with T4 DNA ligase to prepare a conjugated molecule covalently linked together. Recombinant circled DNA is selected by drug resistance derived from pMS 71-17. The transformant of *E. coli* ML4901 is isolated and the strain carrying $Tc^r$ is selected therefrom. Plasmid DNA is isolated from these $Ap^r$ $Tc^r$ strains by conventional methods, and the recombinant plasmid in which both plasmids are ligated can be selected according to the results of agarose-gel electrophoresis.

A plasmid holding in the thus-obtained transformation strain is a shuttle vector which can be replicated in Bacillus *E. coli* and Pseudomonas. $Tc^r$ marker derived from Gram positive bacteria can be expressed in Bacillus. *E. coli* and Pseudomonas, however a Gram $Ap^r$ $Sa^r$ marker derived from Gram negative bacteria and Gram negative resistant marker $Ap^r$ $Sa^r$ does not express in Bacillus. As explained hereinbefore, the drug-resistant gene of *E. coli* transformed in Bacillus is said not to express.

If two different drug resistances are expressed in the foreign plasmid, plasmic DNA is cloned into another resistant DNA to transform resistance to sensitivity, and the transformant can be selected by using another drug resistance.

Preparation of pMS 500-1:

pMS 500 is digested with restriction KpnI and HindIII. By this treatment, $Ap^r$ which cannot be expressed in Bacillus is removed and the resulting smaller vector plasmid can be expressed in *E. coli*, Bacillus and Pseudomonas carrying the $Tc^r$ gene. The thus-obtained vector plasmid is treated with SI nuclease to create blunt ends. Both ends are ligated by T4 DNA ligase and transformed into E. coli, then Tc$^r$ colonies are selected which are confirmed as Ap$^s$. A plasmid is isolated from the Tc$^r$ transformant and the molecular weight of the plasmid DNA is checked by agarose-gel electrophoresis.

Preparation of pMS 502:

In order to insert secondary drug resistance in pMS 500-1, which can express in E. coli, Bacillus and Pseudomonas, pMS 500-1 is digested with restriction enzyme PstI, to prepare linear cohesive ends. Sm$^r$ in pMS 501 can be replicated in E. coli and Bacillus, has a replication origin of E. coli vector pACYC 177 and has a sole cleavage site of PstI at the outer side of the Sm$^r$ gene. pMS 501 is digested with restriction enzyme PstI and covalently linked with pMS 501-1 by treatment with T$_4$ DNA ligase to prepare Tc$^r$ Sm$^r$ transformant pMS 502. Plasmid pMS 502 can be replicated in Bacillus, E. coli and Pseudomonas and provide Tc$^r$ SM$^r$ in these strains.

Preparation of pMS 502-1:

The HindIII and EcoRI sites, which are useful for recombinant gene technology, are located within the Sm$^r$ gene in pMS 502. Plasmid pMS 502 is digested with restriction enzyme AccI to delete regions between two AccI sites, and the remaining sequence is covalently linked at each end by T$_4$ DNA ligase to obtain pMS 502-1.

Preparation of pMS 503:

Two EcoRI sites are located in pMS 502-1.

pMS 502-1 is partially digested with EcoRI. Ap$^r$ in plasmid pTTE 11 (Tc$^r$ Ap$^r$) is derived from Bacillus lickeniformis (J. Bacteriol., pp. 776–786 (1981)) and can be expressed in E. coli and Bacillus. Plasmid pTTE 11 is digested with EcoRI to prepare a DNA fragment containing Ap$^r$, which is covalently linked with pMS 502-1 and transformed in E. coli to prepare the Tc$^r$ Sm$^r$ Am$^r$ carrying plasmid vector pMS 503.

Preparation of pMS 503-1:

Plasmid pMS 503 has a region between two SacI sites on both sides of EcoRI, which is not required for drug resistance and desired replication, and is digested with SacI to delete the fragment and ligate by T$_4$ ligase. Replicant DNA is checked by agarose-gel electrophoresis to prepare plasmid pMS 503-1.

pMS 503-1 per se can be used as a vector, however EcoRI and HindIII sites are located in a region other than the Sm$^r$ gene. Also, PstI is located in a region other than the Ap$^r$ gene.

Preparation of pMS 504:

The restriction enzyme HaeII cleavage site is located in the outer part of the Sm$^r$ gene in pMS 503-1. Plasmid pMS 503-1 is digested with HaeII, ligated by T$_4$ DNA ligase and transformed into E. coli to obtain an Ap$^r$ Tc$^r$ Sm$^s$ strain, in which a PstI site is located on the outer side of the Ap$^r$ gene, so that PstI and BglII sites in the Ap$^r$ gene can be used for insertional inactivation. The other restriction enzyme site preferred for cloning in this plasmid is, for example, HindIII and EcoRI and SstI(SacI). Plasmid pMS 504 can be replicated in E. coli, Pseudomonas and Bacillus together with expressing Ap$^r$ Tc$^r$.

Preparation of pMS 506:

Plasmid pMS 503-1 that has a SacI site located on one side of the Ap$^r$ gene is digested with the restriction enzyme SacI. Next, partial digestion with EcoRI and treatment with SI nuclease are performed to prepare a blunt-ended plasmid, which is ligated with T$_4$ DNA ligase and into E. coli to prepare a TC$^r$ SM$^r$ Ap$^s$ strain. The thus-obtained plasmid has lost HindIII and EcoRI sites outside the Sm$^r$ gene so that HindIII and EcoRI sites in Sm$^r$ can be used for the purpose of insertional inactivation. Other preferred cloning sites are for example singly located PstI and PvuI sites. Plasmid pMS 506 can be replicated in E. coli, Pseudomonas and Bacillus together with expressing Tc$^r$ Sm$^r$.

Preparation of Ap$^r$ Sm$^r$/pMS 505:

Two restriction enzyme PvuII cleavage sites are located at both sides of the Tc$^r$ gene in pMS 503-1, which is digested with PvuII and ligated with T$_4$ DNA ligase and the selected Ap$^r$ Sm$^r$ TC$^s$. EcoRI and HindIII sites in the Sm$^r$ gene of the plasmid thus prepared can be used as insertional inactivation sites, however the PstI site is located differently than the PstI site in the Ap$^r$ gene. So the following treatment is necessary:

Preparation of Ap$^r$ Sm$^r$/pMS 505-1:

Plasmid pMS 505 is digested with PvuI, partially digested with PstI, treated with nuclease BAL31 to remove bases from both ends which are thereafter ligated by T$_4$ DNA ligase and transformed in E. coli. After selecting the Ap$^r$ Sm$^r$ strain, a plasmid DNA isolated from Ap$^r$ Sm$^r$ cells is checked for only one location of a PstI site.

The thus-prepared plasmid pMS tot-1 has an insertional inactivation region for Sm$^r$ genes, such as HindIII and EcoRI sites, and for Ap$^r$ genes, such as PstI and BglII sites. The other restriction enzyme sites located in this plasmid are SacI and AccI. The Ap$^r$ Sm$^r$ strain can be replicated in E. coli and Pseudomonas to express Ap$^r$ Sm$^r$; however, no replication is observed in Bacillus.

ADVANTAGES OF THE INVENTION

The plasmids thus prepared have specific useful features as follows:

1. Large copy numbers and easier selection.

2. Selected markers such as tetracycline resistance, ampicillin resistance and streptomycin resistance or kanamycin resistance and sulfa resistance, in the plasmid can be used.

3. In the plasmid, the sole restriction enzyme cleavage sites, i.e. PstI and BglII and XbaI sites located in the ampicillin-resistant genes, EcoRI and HindIII sites located in streptomycin-resistant genes, XbaI, ClaI, SmaI and HindIII located in kanamycin-resistant genes, and PstI located in sulfa-drug-resistant genes, are located, and are advantageously used. Therefore, cloning of DNA segments can be performed without losing DNA replication activity; moreover, recombinant plasmids can be easily selected by the insertional inactivation method.

4. Plasmids can be transferred into any cells of Bacillus, E. coli and Pseudomonas which are sensitive to antibiotics provided as resistant genes. In any cells of Bacillus, E. coli and Pseudomonas, ampicillin resistance, tetracycline resistance and streptomycin resistance, or those of E. coli and Pseudomonas, ampicillin resistance, kanamycin resistance sulfa drug resistance and streptomycin resistance are expressed, so that in any bacterial cells, the selection of recombinant DNA can be effected by recombinant DNA techniques and insertion methods. Selection of the host cells for the purpose of producing substances by recombinant DNA technology can be freely made.

5. In E. coli cells, the plasmid of the present invention does not mobilize with coexisting transferable plasmids or together with other non-transferable plasmids.

6. The plasmids of the present invention are compatible with vector plasmids pCRI, pBR 322, pACYC 184 and pSC 101 originating from ColE1, pMB1, pISA and R6-5 in *E. coli* host cells.

BRIEF DESCRIPTION OF THE DRAWINGS

FIG. 2B also shows the restriction enzyme cleavage sites of each plasmid in relation to the next plasmid.

EXAMPLES

Figure 1:
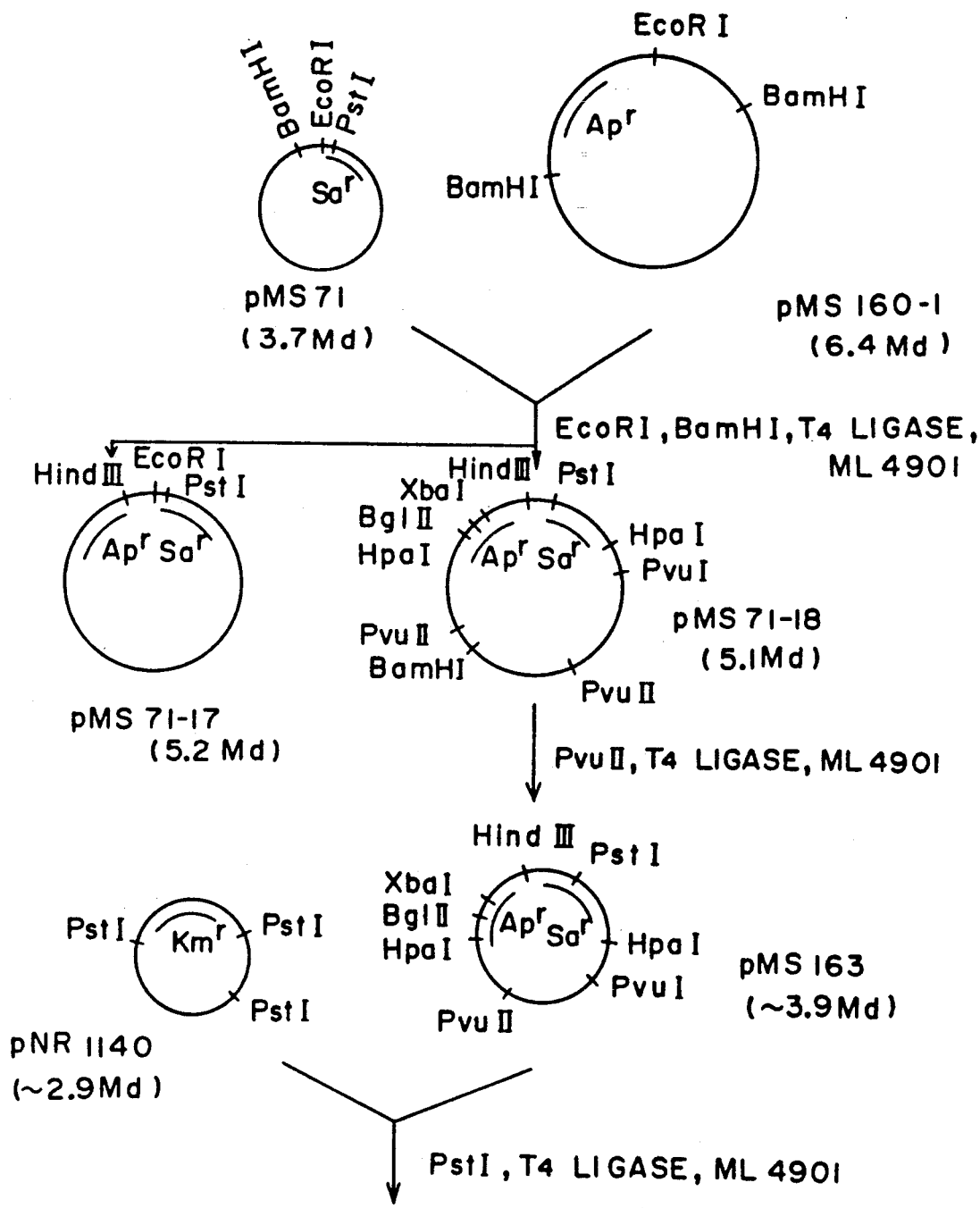
FIGS. 1A and 1B show the restriction sites of versatile vector plasmids of the present invention functional on *E. coli* and Pseudomonas, and processes for the preparation of plasmids.
Figure 1:
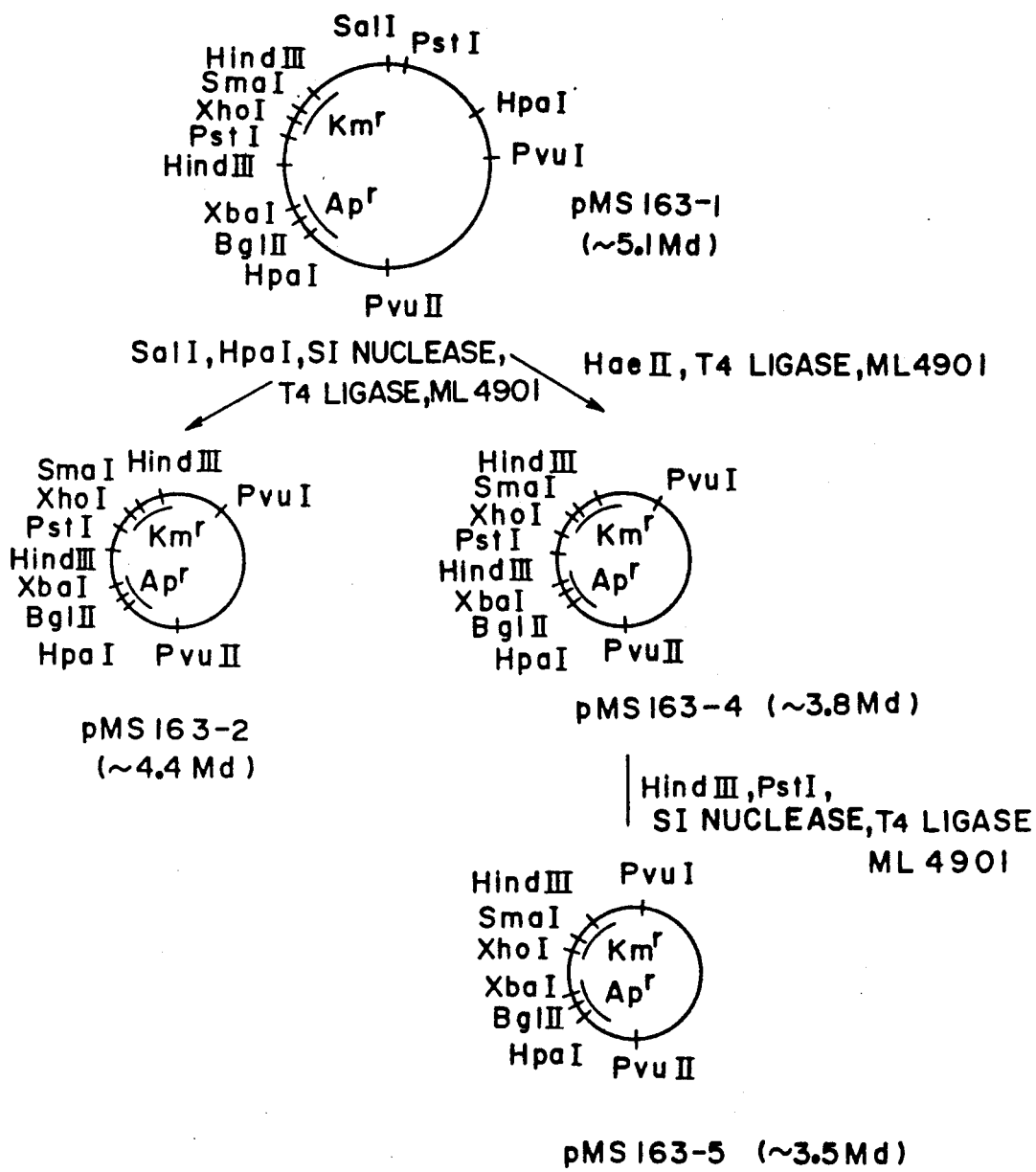
Figure 2:
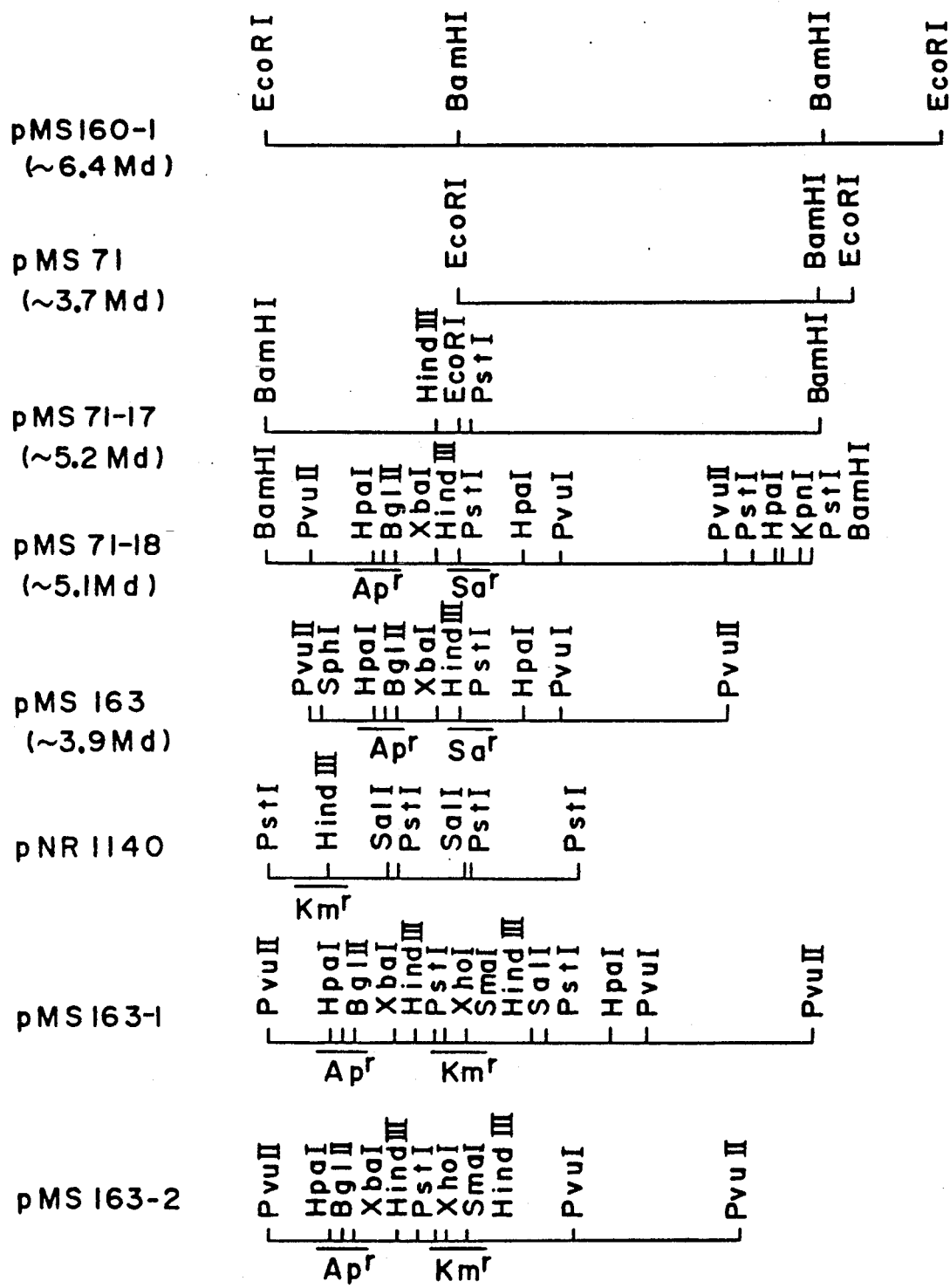
FIGS. 2A and 2B show the restriction enzyme cleavage sites and resistance regions of plasmids in the process of preparing safe and versatile vectors of the present invention.
Figure 3:
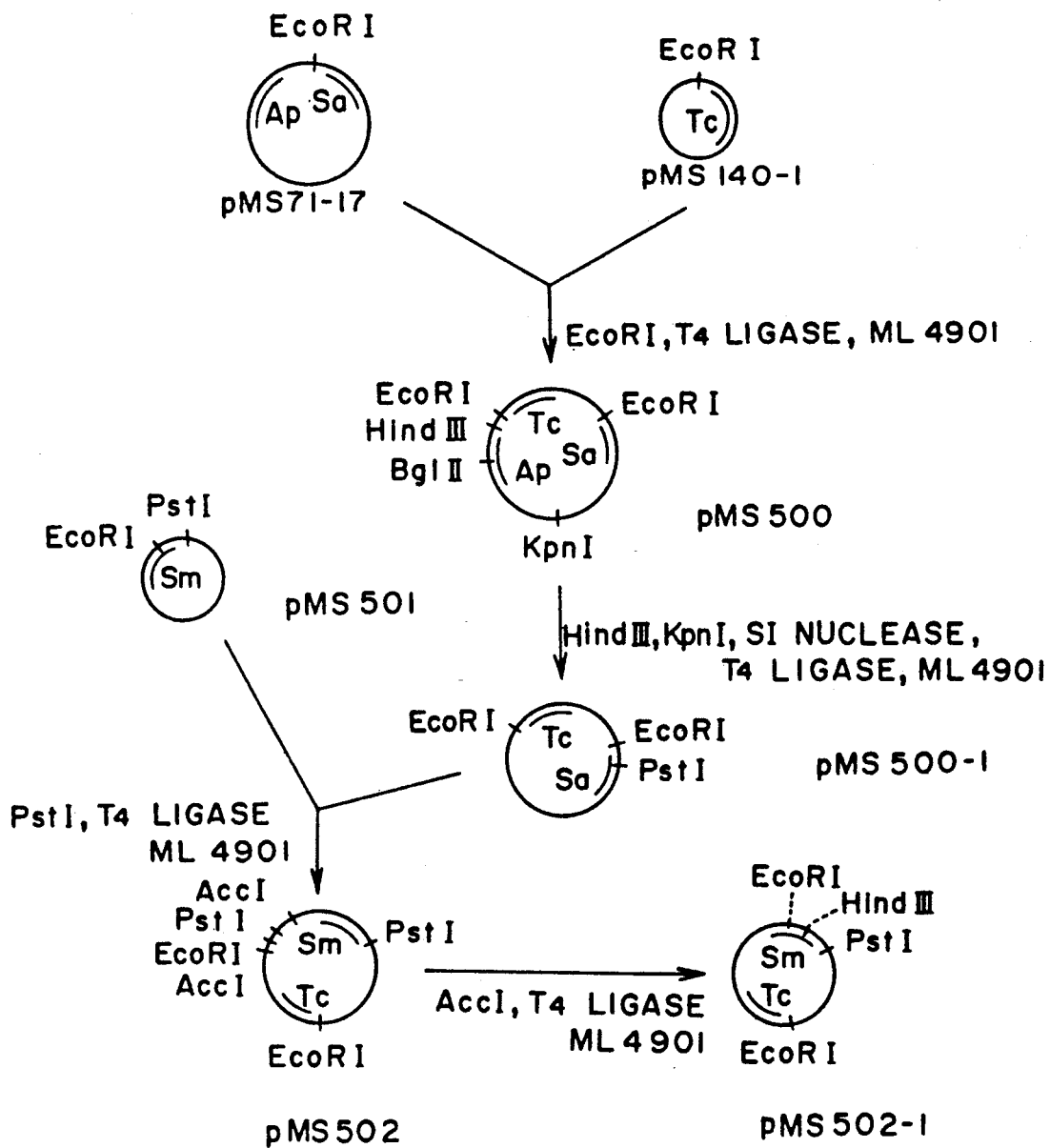
FIG. 3 shows the restriction sites of intermediate plasmids of the present invention and processes for preparation of each plasmid.
Figure 4:
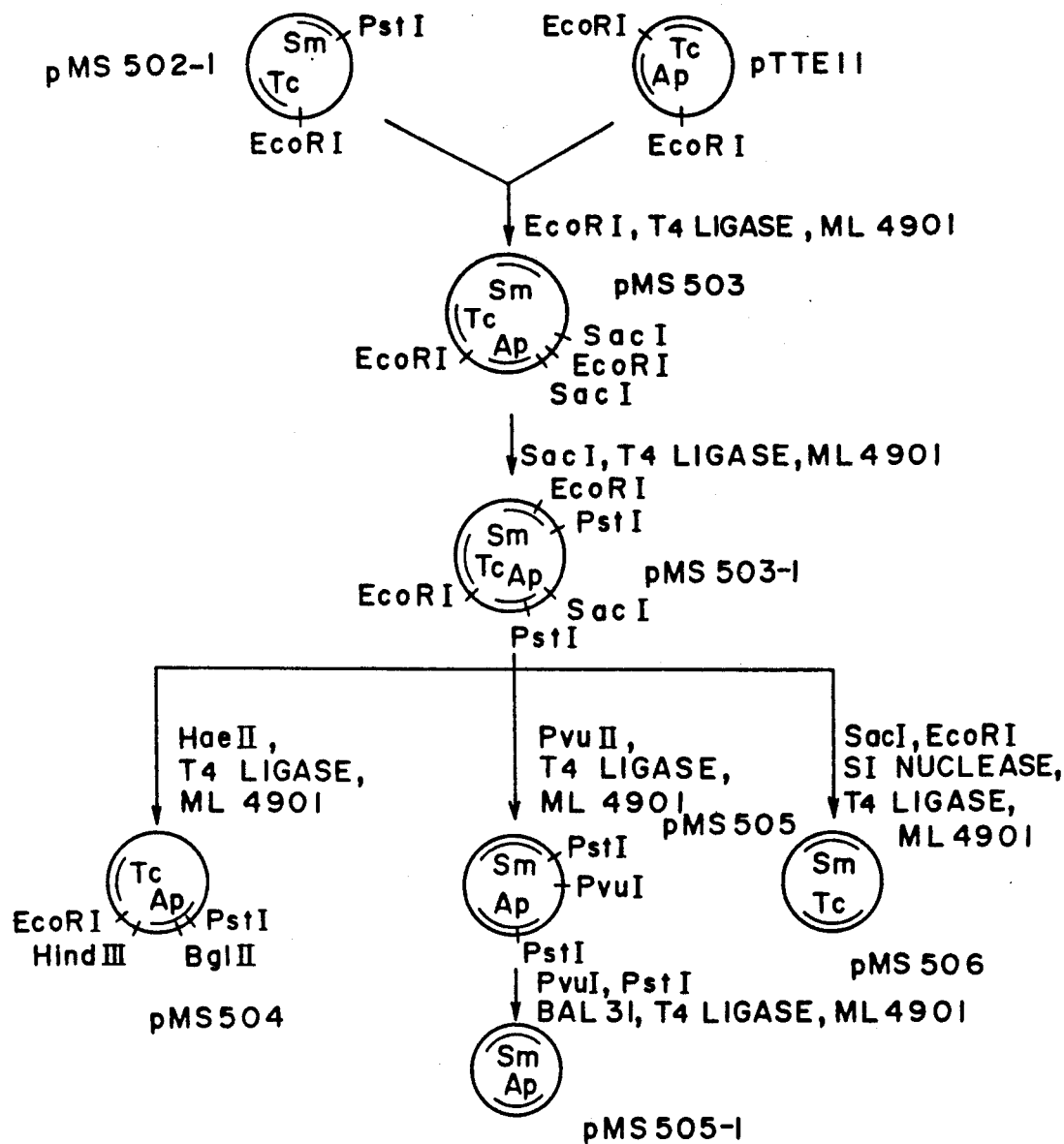
FIG. 4 shows the restriction sites of safe and versatile plasmid vectors of the present invention functional in *E. coli*, Bacillus and Pseudomonas, and a process for the preparation of each plasmid.
Figure 5:
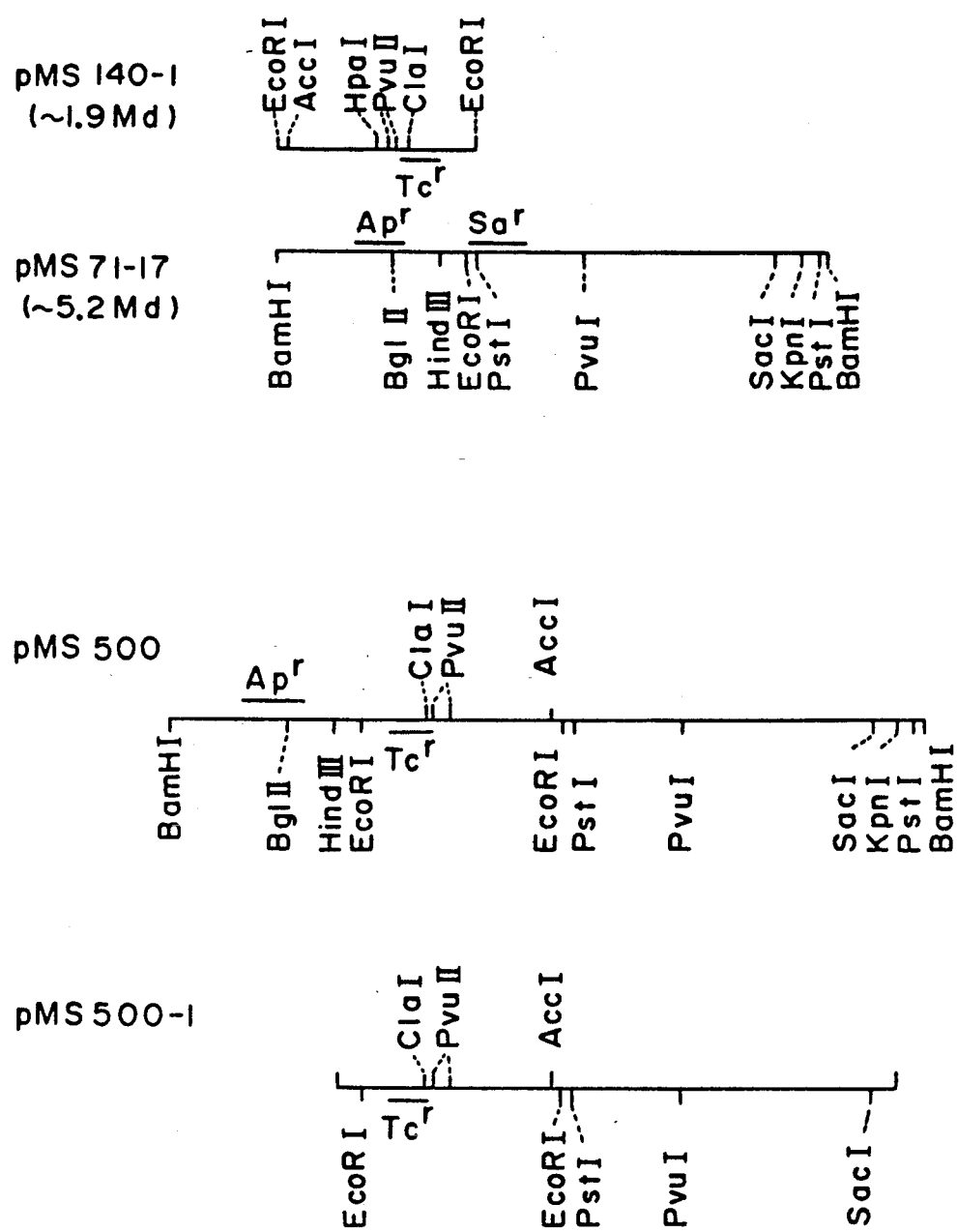
FIGS. 5A, 5B, 5C and 5D show restriction enzyme sites and resistance regions of each plasmid in the process of preparing safe and versatile vector plasmids of the present invention.
Figure 5:
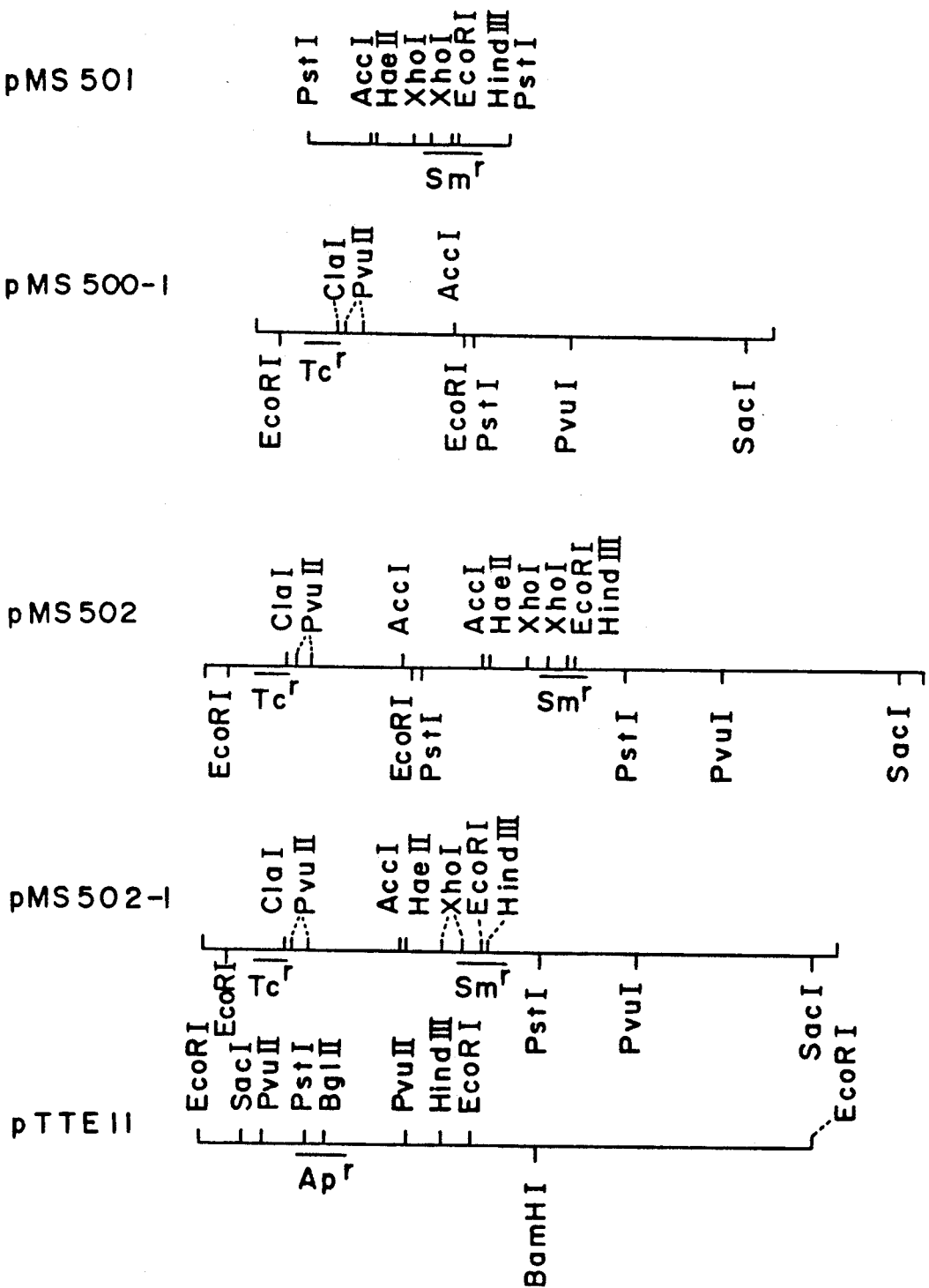
Figure 5:
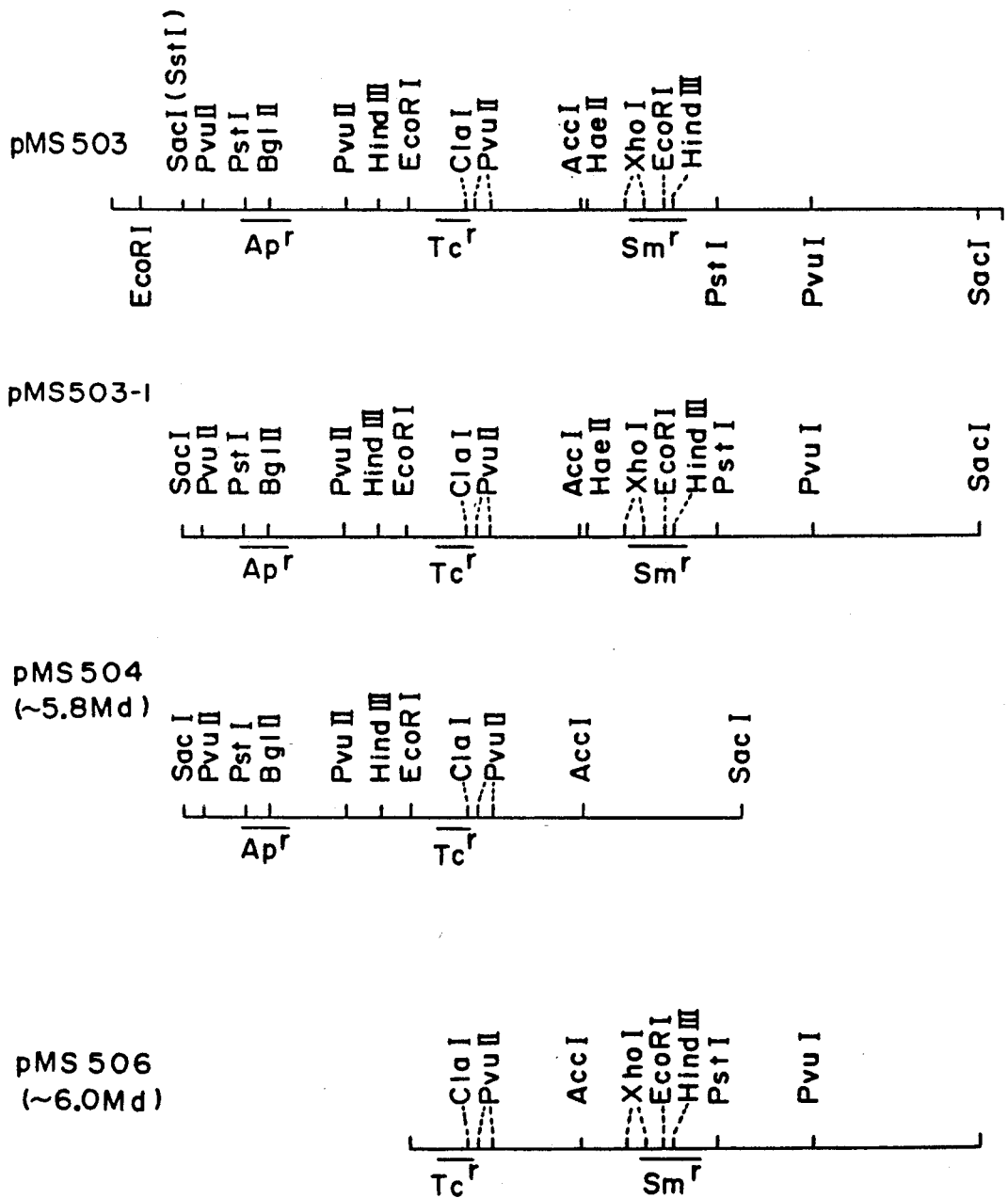
Figure 5:
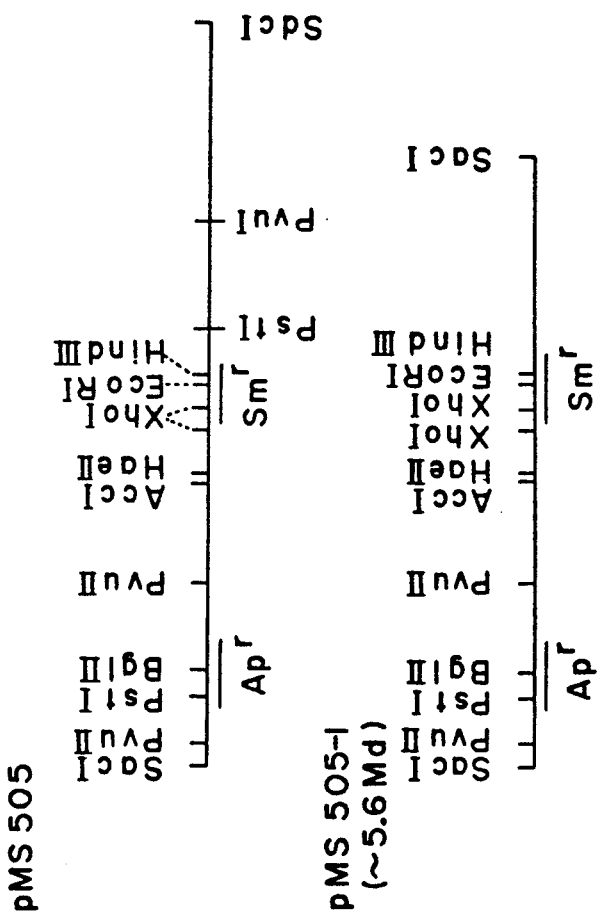

The following examples illustrate the present invention, but are not to be construed as limiting.

In the examples, the buffer solutions for the restriction enzyme and other genetic engineering techniques, the conditions of denaturing the enzyme, the conditions of washing and concentration of DNA solution, and the abbreviations are explained as follows:

1. Buffers for restriction enzyme:

Refer to *Molecular Cloning*, Cold Spring Harbor Laboratory, 1982, p. 104.

| Buffer | NaCl | Tris.Cl(pH 7.5) | MgCl$_2$ | Dithiothreitol |
|---|---|---|---|---|
| Low | 0 | 10 mM | 10 mM | 1 mM |
| Medium | 50 mM | 10 mM | 10 mM | 1 mM |
| High | 100 mM | 50 mM | 10 mM | 1 mM |

2. Other buffers:
a. BAL31-nuclease:
  12 mM CaCl$_2$
  12 mM MgCl$_2$
  0.6 mM NaCl
  20 mM Tris-Hcl (pH 8.0)
b. SI-nuclease:
  0.28M NaCl
  0.05M sodium acetate (pH 4.6)
  4.5 mM ZnSO$_4$
c. T$_4$ DNA ligase:
  10 mM MgCl$_2$
  20 mM dithiothreitol
  50 mM Tris-HCl
  1 mM ATP
  50 μM bovine serum albumin Each buffer is prepared by adding the inorganic salt in distilled water or a buffer specialized for each restriction enzyme to set up fixed concentrations and to sterilize through a millipore filter.

d. TE:
  10 mM Tris-HCl (pH 8.0)
  1 mM EDTA (pH 8.0)

3. Denaturation of enzymes in enzymatic reaction:

PstI and EcoRI: at 70° C. for 5 mins.

Other enzymes: an equal volume of phenol is added to a DNA solution, which is vigorously shaken and centrifuged; and the DNA is transferred into an Eppendorf tube. An equal amount of either is added to the DNA and the material is shaken vigorously and then the upper ether layer is discarded. The same operations are repeated four times in order to remove the enzyme.

4. Washing and concentration of DNA solution:

Ethanol is added, up to a maximum concentration of 70% (w/v), and is allowed to stand at −20° C. for 60 mins., centrifuged at 10,000 r.p.m. for 5 mins. and the upper layer discarded. Prior to ethanol addition, the salts concentration in the DNA solution should be increased, generally by adding 5M NaCl in the amount of 1/50 equivalent and 3M sodium acetate in the amount of 1/10 equivalent.

5. Abbreviations:
  Ap$^r$: ampicillin resistance
  Ap$^s$: ampicillin sensitivity
  Tc$^r$: tetracycline resistance
  Tc$^s$: tetracycline sensitivity
  Sm$^r$: streptomycin resistance
  Sm$^s$: streptomycin sensitivity
  Km$^r$: kanamycin resistance
  Km$^s$: kanamycin sensitivity
  Sa$^r$: sulfa drug resistance
  Sa$^s$: sulfa drug sensitivity

EXAMPLE 1

Preparation of pMS 71 for *Proteus mirabilis* GN5404

Cultured L-broth (1.5 ml) of *Proteus mirabilis* GN5404 stood at 37° C. overnight and then was introduced into an Eppendorf tube and centrifuged at 10,000 r.p.m. for 1 min. The collected cells were washed with TE buffer, centrifuged at 10,000 r.p.m. for 1 min., then the supernatant washing solution was discarded. The cells were suspended by agitation in a Bortex mixer. Cold solution I (50 mM glucose, 10 mM EDTA, 25 mM Tris-HCl buffer, pH 8.0 2 mg/ml lysozyme) (100 μl) was added, stirred and cooled on ice for 30 mins. Solution II (0.2N NaOH, 1% lauryl sulfate) (200 μl) was added thereto mixed by 5–10 turns of the mixer and kept on ice for 5 mins. Cold solution III (3M sodium acetate, pH 4.8) (150 μl) was added, mixed and allowed to stand for 60 The supernatant solution (approx. 400 μl) was centrifuged at 10,000 r.p.m. for 5 mins. and then was transferred to another Eppendorf tube. Twice the volume (800 μl) of cold ethanol was added, and the material was mixed and allowed to stand at −20° C. for 30 mins. After centrifugation at 10,000 r.p.m. for 3 mins., the clear supernatant was discarded and solution IV (0.1M sodium acetate 50 mM, Tris-HCl buffer pH 8.0) (100 μl) was added to dissolve the precipitate. Twice the volume of cold ethanol was added, and the material was mixed, allowed to stand at −20° C. for 10 mins., centrifuged at 10,000 r.p.m. for 3 mins. and the precipitate collected, which was dried in desiccator. The precipitate is dissolved in TE buffer (100 μl) to prepare pMS 71 for transformation.

EXAMPLE 2

Transformation of pMS 71 into *E. coli* ML4901

*E. coli* ML4901 was cultured in L-broth (10 ml) overnight and shake cultured at 37° C. After 3.5 hours culturing OD 560 nm is observed at 0.4, and 5 ml thereof was centrifuged at 3,000 r.p.m. for 10 mins. at room temperature. Then the collected cells were washed with 10 mM NaCl-10 mM Tris-HCl buffer (pH 8.0, 5 ml). The cells collected by centrifugation at 3,000 r.p.m. for 10 mins. were suspended in 75 mM $CaCl_2$-10 mM Tris-HCl buffer (pH 8.0, 5 ml) and allowed to stand at room temperature for 20 mins. The cells were again collected by centrifuge at 3,000 r.p.m. for 10 mins. and were suspended in 75 mM $CaCl_2$-10 mM Tris-HCl buffer (pH 8.0, 5 ml) and allowed to stand on ice for at least 5 mins. to obtain competent cells.

To a plasmid solution (20 μl) obtained in Example 1 which was stored ice cold, in a sterilized small test tube, were added cold competent cells (200 μl). The material was mixed gently and cooled on ice for 20 mins., and then heated for 2 mins. at 42° C. . L-broth was added thereto and the material was shake cultured at 37° C. for 90 mins. After centrifugation at 3,000 r.p.m. for 10 mins., the obtained bacterial cells were washed with BSG 1 ml (NaCl 8.5 g, potassium dihydrogen phosphate 0.3 g, disodium hydrogen phosphate 0.6 g and gelatin 100 mg/l), and resuspended in BSG (1 ml) and a ten-times diluted solution thereof (0.1 ml) was spread on a Lac-BTB agar plate containing sulfonamide (100 μg/ml) and cultured at 37° C. for 24 hours. Transformant cells were twice cultured on a plate containing drugs and the plasmid was separated according to Example 1 and was checked by agarose-gel electrophoresis.

EXAMPLE 3

Identification of the plasmid by agarose-gel electrophoresis 0.8% agarose 1600 (Wako Pure. Chem. Co.) prepared with TEAS buffer (0.05M Tris-HCl, 2 mM EDTA, 18 mM NaCl and 20 mM sodium acetate, pH 8.0) was autocleaved at 120° C. for 10 mins. On cooling at 65° C., the agarose was stirred well without foaming, and was poured gently onto an electrophoresis plate to stand. The DNA sample (10 μl) was mixed with blue dye (tenfold concentrated TEAS buffer 2 ml, bromophenol blue 1.0 mg, sucrose 12 g, 0.5M EDTA 0.8 ml, distilled water up to 20 ml) (1 μl) and poured onto the gel. Upon 10 mins. electrophoresis at 60 mA, the blue dye was observed to have moved into the gel, which was then electrophoresed at 25 mA for 12 hours. The gel was gently removed from the apparatus, stained with ethidium bromide (0.5 μg/ml) for 30 mins. and washed with distilled water. The gel was set on a transilluminator with a UV-filter, and photographed with Polaroid type 57 film.

EXAMPLE 4

Separation of DNA by the Cleared Lysate Method pMS 71/ML4901 obtained in Example 2 was shake cultured at 37° C. overnight in L-broth 200 ml/500 ml in a Sakaguchi flask. The cells were collected by centrifugation at 6,000 r.p.m. at 4° C. for 15 mins. and washed with TE. The collected cells were resuspended in a cold 25% sucrose solution (10 ml) (25% sucrose/50 mM Tris-HCl-1 mM EDTA, pH 8.0). Ribonuclease was added to a final concentration of 20 μg/ml, then the material was transferred to a 30 ml volume centrifugal tube. The reaction volume was mixed using Bortex mixer at the highest speed of revolution. One ml of 1% lysozyme (0.25M Tris-HCl, pH 8.0) was added, and the material was shaken well and cooled on ice for 5 mins.

0.5M EDTA (pH 8.0) (2 ml) was added and the material was gently mixed and cooled on ice 10 mins. Cold triton bacteriolytic solution (0.1% Triton x-100, 50 mM Tris-HCl, 62.5 mM EDTA, pH 8.0) (16 ml) was added and the material was gently mixed, then cooled on ice for 15 mins. The solution was centrifuged at 30,000 r.p.m. for 20 mins. at 4° C. , and the supernatant was separated into a 100 ml flask. Polyethylene glycol-6000 was gently mixed in up to 10% (w/v), and there was added 1/9 equivalent of 5M NaCl. The material was then mixed well and stored at 4° C. overnight. The mixture was centrifuged at 5,000 r.p.m. for 10 mins. at 4° C., the supernatant was discarded, and TE (5.3 ml) was added to the residue to dissolve the DNA. The DNA sample (5.1 ml) was gently mixed with cesium chloride (5 g). After complete dissolution, ethidium bromide (10 mg/ml) (0.1 ml) was added, and the material was mixed well, then centrifuged at 37,000 r.p.m. for 40 hours at 20° C. Over a UV-transilluminator the fluorescent plasmid band in the test tube was collected (1 ml) by puncturing the side of the tube with a needle. Isopropanol saturated with cesium chloride was added in an equal volume and the material was gently shaken to remove the ethidium bromide. This operation was repeated three times to confirm complete removal on the transilluminator UV filter, and then the material was transferred into a dialysis tube and dialyzed against 0.1 SSC (15 mM NaCl, 1.5 mM sodium citrate).

EXAMPLE 5

Preparation of pMS 71-18

To plasmid pMS 71 (40 μl) obtained by the cleared lysate method in Example 4 was added 10 times conc. buffer (500 mM NaCl, 100 mM Tris-HCl, pH 7.5, 100 mM magnesium chloride and 10 mM dithiothreitol) (4 μl) and the restriction enzyme BamHI (2 μl, 3.2 units) was also added, then the material was reacted at 37° C. overnight. pMS 160-1 (40 μl) obtained by the cleared lysate method was reacted with tenfold concentrated buffer (4 μl, hereinafter designated as 10 X conc. medium buffer) in the presence of BamHI (2 μl, 3.2 units) at 37° C. overnight. Samples (10 μl) thereof were checked by agarose-gel electrophoresis to identify the single cleavage of each plasmid. 3M sodium acetate (3 μl) and cold ethanol (80 μl) were added to each plasmid solution and mixed well, and the material was allowed to stand at −80° C. for 30 mins, then centrifuged at 10,000 r.p.m. for 5 mins., the supernatant was discarded and the sediment dried in vacuo. Each sample was dissolved in sterilized distilled water (30 μl) and was reacted with ten times highly concentrated buffer (3 μl, hereinafter designated as 10 X high conc. buffer) and EcoRI (2 μl, 4.0 units) at 37° C. overnight. After checking the cleavage of the plasmids by agarose-gel electrophoresis, 20 μl of each plasmid was mixed, TE-saturated phenol was added thereto and the material was vigorously shaken. The mixture was centrifuged at 10,000 r.p.m. for 1 min., and the upper DNA layer transferred to another Eppendorf tube. Ether (40 μl) was added thereto and mixed well to transfer remaining phenol to the ether layer, then the material was allowed to stand and the upper ether layer was discarded. After repeating this ether treatment four times, ethanol (80 μl) was added to the DNA layer and the material was allowed to stand at −80° C. for 30 mins. The mixture was centrifuged at 10,000 r.p.m. for 5 mins. to separate a supernatant solution, which was discarded, and the sediment was dried in vacuo. Dried DNA was dissolved by adding T4 DNA ligase buffer (30 μl), and T4 DNA ligase (1 μl) was added, and the material was allowed to react at 16° C. overnight. The reaction mixture (20 μl) was added to competent cells (200 μl) of ML4901 prepared in the same way as in Example 2 for transformation to obtain transformant Sa$^r$Ap$^r$.

Agarose-gel electrophoresis and analysis using a restriction enzyme indicated that the resulting transformant Sa$^r$Ap$^r$ contains a mutant lacking 0.1 Md fragment including the EcoRI site. The former was designated as pMS 71-17 (5.2 Md) and the latter as pMS 71-18 (5.1 Md).

EXAMPLE 6

Preparation of pMS 163

A mixture of pMS 71-18 (30 μl), 10X med. conc. buffer (3 μl) and PvuII (2 μl, 5.0 units) was reacted at 37° C. overnight. Samples (10 μl) thereof were checked by agarose-gel electrophoresis for cleavage of the plasmid. The reaction mixtures were subjected to phenol treatment and ether treatment as in Example 5, and thereafter 3M sodium acetate (2 μl) and cold ethanol (60 μl) were added and well mixed, and the material was then allowed to stand at −80° C. for 30 mins. The mixtures were centrifuged at 10,000 r.p.m. for 5 mins., the supernatant discarded, and the precipitate dried in vacuo. The precipitate was dissolved in a buffer (40 μl), for T4 DNA ligase), ligated with T4 DNA ligase, and thereafter was treated as in Example 5 to obtain transformant Sa$^r$Ap$^r$. Ten strains were treated the same as in Example 1 to extract DNA analyzed by agarose-gel electrophoresis. Plasmids of all 10 strains were the same size (3.9 Md) which were designated as pMS 163.

EXAMPLE 7

Preparation of pMS 163-1

Mixtures of pMS 163 (30 μl), 10X med. conc. buffer (3 μl) and PstI (2 μl, 5.6 units) were reacted at 30° C. overnight. Also mixtures of pNR 1140 (30 μl), 10X med. conc. buffer (3 μl) and PstI (1 μl, 2.8 units) were reacted at 30° C. overnight. Each DNA was analyzed by agarose-gel electrophoresis to identify the cleavage site of PstI, and thereafter both DNA solutions (each 20 μl) were mixed and treated with phenol and ether the same as in Example 5. Also, ethanol precipitation and ligation by T4 DNA ligase were carried out as in Example 5 to perform transformation. The potential transformants were spread on a Lac-BTB agar plate containing ampicillin 25 μg/ml. The colonies that appeared after incubation overnight at 37° C. were checked for resistances to kanamycin 25 μg/ml and sulfonamide 50 μg/ml to obtain a strain resistant to ampicillin and kanamycin and sensitive to sulfonamide. Plasmide DNA was isolated by the cleared lysate method. The resulting plasmid DNA was mixed with pNR 1140 DNA, cleaved with PstI and ligated together forming pMS 163-1.

EXAMPLE 8

Preparation of pMS 163-2

Plasmid pMS 163-1 (50 μl), 10X high conc. buffer (5 μl) and SalI (1.5 μl, 1.5 unit) were mixed and reacted at 37° C. overnight. A 10 μl portion thereof was electrophoresed on agarose gel to identify the cleavage of the plasmid, whereafter the reaction mixture was mixed with cold ethanol (100 μl) and allowed to stand at −80° C. for 30 mins., then centrifuged at 10,000 r.p.m. for 5 mins. to collect a precipitate which was dried in vacuo. Nuclease SI (0.5 μl, 250 units) was added to the precipitate dissolved in a buffer (50 l) for SI nuclease and reacted at 30° C. for 30 mins TE-saturated phenol (50 μl) was added thereto, the material was vigorously stirred, centrifuged at 10,000 r.p.m. for 1 min. and the upper aqueous layer was transferred to another Eppendorf tube. Water-saturated ether (50 μl) was added, the material was stirred, allowed to stand and the upper ether layer was discarded. This ether treatment was repeated four times. Cold ethanol was added thereto and the material was again allowed to stand at −80° C. for 30 mins., then centrifuged at 10,000 r.p.m. for 5 mins., and the precipitate was collected and dried in vacuo. The precipitate was dissolved in sterilized distilled water (40 μl), to which was added 10X low conc. buffer (4 μl) and Hpal (1 μl, 0.5 unit), and the mixture was reacted at 37° C. for 30 mins. Treatment with phenol, ether and ethanol precipitation, as above, were performed and the material was dried in vacuo, then ligase treatment and transformation were performed as in Example 5. Colony growth on Lac-BTB agar containing ampicillin (25 μg/ml) was confirmed and had kanamycin resistance. DNA comprising 50 strains thereof was analyzed by agarose-gel electrophoresis to yield 15 strains having a smaller size plasmid than pMS 163-1.

EXAMPLE 9

Preparation of pMS 163-4

Plasmid DNA of pMS 163-1 (20 μl) 10X low conc. buffer (2 μl) and HaeII (0.5 μl, 0.2 unit) were mixed and reacted at 37° C. for 30 mins. After treatment with phenol and ethanol, 3M sodium acetate (2 μl) was added. Then after ethanol precipitation, ligase reaction and transformation were performed as in Example 5 to select ampicillin- and kanamycin-resistant strains. 50 plasmid strains thereof were analyzed by agarose-gel electrophoresis to yield lower molecular weight plasmids.

EXAMPLE 10

Preparation of pMS 163-5

Plasmid pMS 163-4 (50 μl), 10X med. conc. buffer (5 μl) and PstI (2 μl, 5.6 units) were mixed and reacted at 30° C. overnight, then checked for cleavage by agarose-gel electrophoresis. HindIII (1 μl, 1.2 unit) was added therein, the material was reacted at 37° C. for 30 mins., and subjected to phenol and ether treatment. Then 3M sodium acetate (4 μl) was added thereto and the material was treated with ethanol, then digested with SI nuclease as in Example 8, and subjected to treatments with phenol, ether and ethanol precipitation. The precipitate thus obtained was dissolved in ligase buffer and reacted with T4 DNA ligase. Again, treatments with phenol and ether and ethanol precipitation were carried out. The thus-obtained precipitate was dissolved in sterilized distilled water (40 μl), mixed with 10X med. conc. buffer (4 μl) and PstI (2 μl) and reacted at 37° C. for 2 hours. The reaction mixture contained competent cells of ML4901 strain and was spread on Lac-BTB agar medium containing kanamycin 25 μg/ml. Three strains of Km$^r$ Ap$^r$ were obtained and two strains thereof were suitable.

EXAMPLE 11

Preparation of pMS 500 from pMS 71-17 and pMS 140-1

A 10X high conc. buffer (5 μl, for a restriction enzyme) and EcoRI (0.5 μl, 2.5 units) were added to pMS 140-1 (50 μl, 1 μg DNA) and the mixture was reacted at 37° C. overnight. A pMS 17-17 (50 μl) was treated with EcoRI. Both reaction mixtures were combined and treated at 70° C. for 5 mins. to stop the reaction, then 99.5% ethanol (220 μl) was added thereto, and the material was mixed and allowed to stand at 20° C. for 60 mins. The mixture was centrifuged at 10,000 r.p.m. for 5 mins., the supernatant solution was discarded, and the remainder was dried in vacuo. Buffers for $T_4$-DNA ligase (50 μl) and $T_4$-DNA ligase (0.2 μl, 1 unit) were added thereto and the mixture was reacted at 16° C. overnight. An E. coli competent cell suspension (200 μl) was added thereto and the material was reacted on ice for 20 mins. and heated at 42° C. for 2 mins. L-broth (1 ml) was added, and the material was shake cultured at 37° C. for 90 mins., and centrifuged at 3,000 r.p.m. for 10 mins. The collected cells were washed twice with BSG (1 ml) and spread on Lac-BTB agar medium containing ampicillin 25 μg/ml. After incubating at 37° C. overnight, the grown colonies were spread on Lac-BTB medium containing tetracycline 12.5 μg/ml and ampicillin 25 μg/ml using sterilized sticks, and colonies grown on agar plates were treated twice on the same drug concentration agar medium to obtain an $Ap^r Tc^r$ strain.

EXAMPLE 12

Preparation of pMS 500-1 from pMS 500

A plasmid was obtained from a strain carrying plasmid pMS 500 by the previously described method. Prepared plasmid (20 μl), 10X low conc. buffer (2 μl) and KpnI (0.5 μl, 4.5 units) were mixed and reacted at 30° C. overnight. 5M NaCl (0.25 μl) and HindIII (0.5 μl, 6.0 units) were added thereto and the material was reacted at 37° C. for 5 hours. Then 3M sodium acetate (2 μl) and 99.5% ethanol (50 μl) were added and the material was mixed, then allowed to stand at −20° C. for 60 mins. The reaction mixture was centrifuged at 10,000 r.p.m. for 5 mins., the supernatant solution was discarded and the remainder was dried in vacuo. SI nuclease (0.5 μl, 29 units) was added to the precipitate suspended in a buffer (50 μl, for SI nuclease), and the mixture was reacted at 30° C. for 30 mins., whereafter TE-saturated phenol (50 μl) was added and the mixture was stirred vigorously with a Bortex mixer (approx. 5 sec.), then centrifuged at 10,000 r.p.m. for 1 min. and the upper aqueous layer was collected. Water-saturated ether (50 μl) was added thereto, and the material was stirred (approx. 2 sec.) and allowed to stand 1 min., and the upper ether layer was discarded. The ether treatment was repeated four times, and to the resulting aqueous layer (approx. 50 μl) was added 99.5% ethanol (120 μl) and the material was allowed to stand at −20° C. After one hour the solution was centrifuged at 10,000 r.p.m. for 5 mins. The precipitate was washed with 70% ethanol (100 μl) and again centrifuged, discarding the supernatant solution, after which the solids were dried in vacuo, suspended in a buffer for $T_4$ ligase, $T_4$ DNA ligase (0.2 μl, 10 units) was added and the material was reacted at 16° C. overnight. Transformation into E. coli was performed as in Example 11, and the transformant was spread on Lac-BTB medium containing tetracycline 12.5 μg/ml, then incubated at 37° C. overnight. Colonies grown on the said medium which could not grow in ampicillin (25 μg/ml) were selected to obtain a $Tc^r Ap^r$ strain.

EXAMPLE 13

Preparation of pMS 502 from pMS 500-1 and pMS 501

A 10X med. con. buffer (2 μl) and PstI (1 μl, 5 units) were added to pMS 500-1 (20 μl) and the mixture was reacted at 30° C. Then 10X med. con. buffer (5 μl) and PstI (1 μl, 5 units) were added to pMS 501 (50 μl) and the mixture was reacted at 30° C. overnight. Both reaction mixtures were combined, treated at 70° C. for 5 mins. to denature the enzyme, then were treated as in Example 11, for example by ethanol precipitation, $T_4$ DNA ligase treatment and transformation into E. coli. The thus-obtained strains were selected by a Lac-BTB medium containing tetracycline 12.5 μg/ml, and the colonies grown on this medium were spread on a Lac-BTB medium containing streptomycin 6.25 μg/ml, whereby there was selected the strain resistant to tetracycline 12.5 μg/ml and streptomycin 6.25 μg/ml to obtain a $Tc^r Sm^r$ strain.

EXAMPLE 14

Preparation of pMS 502-1 from pMS 502

A 10X med. conc. buffer (2 μl) and AccI (2 μl, 1.4 unit) were added to pMS 502 (20 μl) and the mixture was reacted at 37° C. overnight. Subsequent operations proceeded as in Example 12, i.e. phenol treatment, ether treatment (5 times), ethanol precipitation, $T_4$ DNA ligase treatment and transformation into E. coli. The resulting strains were selected by resistance to tetracycline 12.5 μg/ml. The plasmid isolated therefrom was checked by agarose-gel electrophoresis and the plasmid smaller than plasmid pMS 502 was selected, to obtain pMS 502-1.

EXAMPLE 15

Preparation of pMS 503 from pMS 502-1 and pTTE11

A 10X high conc. buffer (2 μl) and EcoRI (0.5 μl, 0.25 unit) were added to pTTE11 (20 μl) and the mixture was reacted at 37° C. overnight. A 10X high conc. buffer (2 μl) and EcoRI (1 μl, 0.5 unit) were added to pMS 502-1 (20 μl) and the mixture was reacted at 37° C. for 10 mins. Both plasmid solutions were combined, heated at 70° C. for 5 mins., and subsequent operations were performed as in Example 11 for transformation into E. coli. Colonies were selected for growth on a Lac-BTB medium containing streptomycin 3.13 μg/ml and for secondary resistances to ampicillin 25 μg/ml and tetracycline 12.5 μg/ml to obtain a $Tc^r Sm^r Ap^r$ strain. The plasmid was checked by agarose-gel electrophoresis to determine that the original pTTE11 had not contaminated the preparation.

EXAMPLE 16

Preparation of pMS 503-1 from pMS 503

A 10X low conc. buffer (2 μl) and SacI (0.5 μl, 1.25 unit) were added to pMS 503 (20 μl) and the mixture was reacted at 37° C. overnight. Phenol (20 μl) and ether (20 μl, 4 times) treatments, ethanol concentration, reaction with $T_4$ DNA ligase and transformation into E. coli were performed as in Example 5. Colonies selected by streptomycin 3.13 μg/ml were confirmed to grow on tetracycline 12.5 μg/ml and ampicillin 25 μg/ml. The plasmid isolated from the colonies was identified by agarose-gel electrophoresis as a smaller plasmid.

EXAMPLE 17

Preparation of pMS 504 from pMS 503-1

A 10X low conc. buffer (2 μl) and HaeII (0.5 μl, 4 units) were added to pMS 503-1 (20 μl) and the mixture was reacted at 37° C. overnight. The subsequent procedure was the same as in Example 16. Colonies were selected in ampicillin 25 μg/ml, and grown colonies were further selected by growth on tetracycline 12.5 μg/ml, and no-growth on streptomycin 3.13 μg/ml to obtain an Ap$^r$ Tc$^r$ Sm$^r$ strain. Plasmids thereof were identified by agarose-gel electrophoresis as in Example 16.

EXAMPLE 18

Preparation of pMS 506 from pMS 503-1

A 10X low conc. buffer (5 μl) and SacI (1.5 μl, 2.5 units) were added to pMS 503-1 (20 μl) and the mixture was reacted at 37° C. overnight. A 10X high conc. buffer (6 μl) was added thereto, and there was further added EcoRI (1 μl, 0.5 unit), then the material was reacted at 37° C. for 15 mins. and thereafter heated at 70° C. for 5 mins. to stop the reaction. 99.5% ethanol (140 μl) was added thereto and the material was allowed to stand at −20° C. for 60 mins. Further treatments by SI nuclease, phenol, ether (4 times) and ethanol, and T$_4$ DNA ligase treatment were as in Example 12 as was the transformation into *E. coli*. Colonies grown on Lac-BTB medium containing streptomycin 3.13 μg/ml were selected, and this strain was checked for resistance to tetracycline to obtain a Sm$^r$ Tc$^r$ Ap$^s$ strain. The plasmid isolated according to the method described in Example 1 was identified by agarose-gel electrophoresis.

EXAMPLE 19

Preparation of pMS 505 from pMS 503-1

A 10X med. conc. buffer (2 μl) and PvuII (0.5 μl, 0.5 unit) were added to pMS 503-1 (20 μl) and the mixture was reacted at 37° C. for 30 mins. Phenol treatment, ether treatment, ethanol precipitation and T$_4$ DNA ligase treatment were performed as in Example 12 as was transformation into *E. coli*. Colonies grown on Lac-BTB medium containing ampicillin 25 μg/ml were selected and further identified as to growth on streptomycin 6.25 μg/ml and no-growth on tetracycline 12.5 μg/ml to obtain an Ap$^r$ Sm$^r$ Tc$^s$ strain.

EXAMPLE 20

Preparation of pMS 505-1 from pMS 505

A 10X high conc. buffer (3 μl) and PvuII (1 μl), 4 units) were added to pMS 505 (30 μl) and the material was reacted at 37° C. overnight. 99.5% ethanol (70 μl) was added thereto and the mixture was allowed to stand at −20° C. for 60 mins. The reaction mixture was centrifuged at 10,000 r.p.m. for 5 mins., the supernatant discarded and the DNA dried in vacuo. Sterilized water (30 μl), 10X med. conc. buffer (3 μl) and PvuII (1 μl, 0.5 unit) were added thereto and the mixture was reacted at 30° C. for 30 mins. The reaction mixture was heated at 70° C. for 5 mins., 3M sodium acetate (3 μl) was added thereto, then 99.5% ethanol 70 μl, and the mixture was allowed to stand at −20° C. for 60 mins. The reaction mixture was centrifuged at 10,000 r.p.m. for 5 mins., the supernatant discarded and the precipitate dried in vacuo. The precipitate was suspended in a buffer for BAL31 (50 μl), and BAL31 (0.5 μl, 1.25 units) was added thereto, and the mixture was reacted at 30° C. for 10 mins. TE-saturated phenol (50 μl) was added and the material was vigorously stirred with a Bortex mixer, then centrifuged at 10,000 r.p.m. for 1 min., and the upper aqueous layer was collected and treated with ether (5 times), ethanol and T$_4$ DNA ligase as in Example 12. Transformation into *E. coli* was performed as in Example 11 and colonies were selected to grow on Lac-BTB medium containing ampicillin 25 μg/ml. The grown colonies were confirmed as to streptomycin 6.25 μg/ml resistance to obtain an Ap$^r$ Sm$^r$ strain. The plasmid isolated from the Ap$^r$ Sm$^r$ strain according to the method described in Example 1 was identified as smaller than pMS 505. Further PstI digestion indicated a single cleavage site.

EXAMPLE 21

Transformation of vector plasmid into Bacillus and Pseudomonas

Plasmid vector (25 μl) obtained according to the description in *Method of Assaying Drug Sensitivity*, Ed. Mitsuhashi, pp. 42–48, was used for transformation into *Bacillus subtilis, Pseudomonas aeruginosa* and *Pseudomonas putida*.

(A) *Bacillus subtilis* (CRK 3000):

Plasmid pMS 504 or 506 (25 μl) obtained in the previous examples was mixed with competent cells of *Bacillus subtilis* (CRK 3000) (200 μl) and the mixture was shaken at 37° C. for 30 mins. The mixture was spread on a heart infusion agar plate containing tetracycline 6.25 μg/ml and incubated at 37° C. overnight, then the grown colonies were cultured (pure culture) on a medium containing tetracycline 1.25 μg/ml. This strain was inoculated in an assay medium for sensitivity test broth (Nissui Co.) and cultured at 37° C. for 18 hours. The cultured broth was diluted with BSG to 10$^5$–10$^6$ cells/ml, and 5 μl thereof was inoculated on an agar plate containing each a drug with various concentration by using a micro-planter. The plates were incubated at 37° C. for 18 hours and the growth of the colonies was checked. The results are shown in Table 1.

TABLE 1

| | MIC (μg/ml) | | | iodine method* |
|---|---|---|---|---|
| | Tc | SM | Ap | |
| pMS 504/CRK3000 | 100 | 6.25 | 0.025 | +++ |
| pMS 506/CRK3000 | 100 | 100 | 0.025 | — |
| CRK | 1.6 | 6.25 | 0.025 | — |

*according to the method in Protein Nucleic Acid Enzyme, 23 (5), (1978).

The above transformants were identified by the nitrocephine method showing pMS 504 producing a β-lactamase.

(B) *Pseudomonas aeruginosa* and *Pseudomonas putida*

Plasmid pMS 505-1 or pMS 506 (25 μl) obtained in the previous examples was mixed with competent cells (200 μl) of *Pseudomonas aeruginosa* or *Pseudomonas putida* and the material was reacted at 0° C. for 60 mins., thereafter heated at 42° C. for 2 mins. L-broth (1 ml) was added thereto and the material was incubated at 37° C. for 90 mins. The cultured broth was centrifuged at 3,000 r.p.m. for 10 mins., washed twice with BSG, then BSG (0.5 ml) was added thereto. The strains were selected by spreading on a Lac-BTB medium containing streptomycin 12.5 μg/ml, and this was twice repeated with the pure culture medium containing streptomycin 25 μg/ml to obtain transformed pure culture strains of *Pseudomonas aeruginosa* and *Pseudomonas putida*.

The MIC (μg/ml) of these strains ($10^6$ cells/ml) is shown in Tables 2 and 3.

TABLE 2

| MIC on *Pseudomonas aeruginosa* | | | |
|---|---|---|---|
| | Tc | SM | Ap |
| pMS 506/*P. aerginosa* | 50 | 100 | 12.5 |
| pMS 505-1/*P. aerginosa* | 6.25 | >200 | >1600 |
| *P. aeruginosa* PAO 2142 | 6.25 | 1.6 | 12.5 |

TABLE 3

| MIC on *Pseudomonas putida* | | | |
|---|---|---|---|
| | Tc | SM | Ap |
| pMS 506/*P. putida* | 50 | 200 | 100 |
| pMS 505-1/*P. putida* | 1.6 | >200 | >1600 |
| *P. putida* In 1126 | 1.6 | 1.6 | 100 | the MIC of the host cells *E. coli* used is shown in Table 4.

TABLE 4

| MIC on *E. coli* | | | |
|---|---|---|---|
| | Sm | Tc | Ap |
| pMS 504/ML4901 | 0.4 | 6.25 | 800 |
| pMS 506/ML4901 | 100 | 6.25 | 1.6 |
| pMS 505-1/ML4901 | 100 | 0.8 | >1600 |
| *E. coli* ML4901 | 0.4 | 0.8 | 1.6 |

What is claimed is:

1. Versatile recombinant DNA cloning vector having a first replication origin functional in *Escherichia coli* and *Pseudomonas aeruginosa*, and a second replication origin functional in *Bacillus subtilus*, said versatile recombinant DNA cloning vector also having genes expressing resistance to two types of antibiotic in each of said three species of microorganisms, after introduction into transformable host cells of said microorganisms which are sensitive to antibiotics, said vector being non-mobilizable in *E. coli* cells with coexisting transferable plasmids or together with other non-transferable plasmids.

2. The vector according to claim 1, wherein the replication origin functional in *Bacillus subtilis* is a restriction fragment of a plasmid pMS 140-1 of *Bacillus cereus*, and the replication origin functional in *Escherichia coli* and *Pseudomonas aeruginosa* is a restriction fragment of a plasmid pMS 71 of *Proteus mirabilis*.

3. The vector according to claim 2, wherein in said plasmid two kinds of antibiotic-resistant genes are present selected from the group consisting of an ampicillin-resistant gene, a streptomycin-resistant gene and a tetracycline-resistant gene.

4. The vector according to claim 3, wherein a selected marker gene is originated from a chromosome or plasmid of Gram positive bacteria.

5. Transformed host cells selected from the group consisting of *Bacillus subtilis, Escherichia coli, Pseudomonas aeruginosa* and *Pseudomonas putida*, said transformed host cells being transformed with the recombinant DNA vector of claim 1, wherein at least one of said replication origins within said vector is functional in said host cells.

6. A versatile recombinant DNA cloning vector pMS 504 (Ap'Tc').

7. A versatile recombinant DNA cloning vector pMS 505-1 (Ap'Sm').

8. The vector according to claim 1, wherein said vector is not mobilizable in association with pMS 76.

* * * * *